United States Patent [19]

Liepmann et al.

[11] 4,402,981

[45] Sep. 6, 1983

[54] N₁-ACYL-N₂-PHENYL-DIAMINO-PROPANOLS AND PHARMACEUTICAL COMPOSITIONS THEREOF AND PROCESSES FOR THEIR PREPARATION

[75] Inventors: Hans Liepmann; Rolf Hueschens, both of Hanover; Wolfgang Milkowski, Burgdorf; Horst Zeugner; Henning Heinemann, both of Hanover; Klaus-Ullrich Wolf, Haenigsen; Insa Hell; Reinhard Hempel, both of Hanover, all of Fed. Rep. of Germany

[73] Assignee: Kali-Chemie Pharma, GmbH, Hanover, Fed. Rep. of Germany

[21] Appl. No.: 243,746

[22] Filed: Mar. 16, 1981

Related U.S. Application Data

[60] Continuation of Ser. No. 67,715, Aug. 17, 1979, abandoned, which is a division of Ser. No. 900,998, Apr. 28, 1978, Pat. No. 4,191,770.

[30] Foreign Application Priority Data

May 10, 1977 [DE] Fed. Rep. of Germany ........ 2720915
May 10, 1977 [DE] Fed. Rep. of Germany ........ 2720968

[51] Int. Cl.³ ................ C07C 103/38; C07C 103/78; A61K 31/165
[52] U.S. Cl. .................... 424/324; 260/404.5; 564/123; 564/170; 564/176; 564/182; 564/188; 564/189; 564/190; 564/207; 564/212; 564/213; 564/220

[58] Field of Search .............. 260/404.5 R, 404.5 F; 564/212, 213, 207, 188, 123, 170, 176, 182, 189, 190, 220; 424/324

[56] References Cited

U.S. PATENT DOCUMENTS 2,658,076 11/1953 Krimmel .................. 260/558 R
3,906,040 9/1975 Vincent et al. ............. 260/558 R
3,998,809 12/1976 Milkowski et al. ......... 260/558 R X
4,059,621 11/1977 Vincent et al. ............. 260/559 R X
4,216,167 8/1980 Milkowski et al. ............ 564/176

FOREIGN PATENT DOCUMENTS 2411885 9/1974 Fed. Rep. of Germany ...... 564/220

*Primary Examiner*—Thomas A. Waltz
*Attorney, Agent, or Firm*—Schwartz, Jeffery, Schwaab Mack, Blumethal & Koch

[57] ABSTRACT

$N_1$-acyl-$N_2$-phenyl-1,3-diaminopropan-2-ols are disclosed which possess ulcer-inhibiting activities.

Further disclosed are pharmaceutical compositions which are effective in the treatment and prophylaxis of ulcers and which comprise as a pharmacologically active ulcus-inhibiting ingredient $N_1$-acyl-$N_2$-phenyl-1,3-diaminopropan-2-ols, or a pharmaceutically acceptable acid addition salt thereof, and a pharmaceutically acceptable diluent.

Further disclosed are processes for the preparation of the $N_1$-acyl-$N_2$-phenyl-1,3-diaminopropan-2-ols.

47 Claims, No Drawings

$N_1$-ACYL-$N_2$-PHENYL-DIAMINOPROPANOLS AND PHARMACEUTICAL COMPOSITIONS THEREOF AND PROCESSES FOR THEIR PREPARATION This is a continuation of application Ser. No. 067,715 filed Aug. 17, 1979, now abandoned which in turn is a dividsion of Ser. No. 900,998 filed Apr. 28, 1978 now U.S. Pat. No. 4,191,770.

BACKGROUND OF THE INVENTION

The present invention relates to new $N_1$-acyl-$N_2$-phenyl-1,3-diaminopropan-2-ol derivatives, processes for their preparation and pharmaceutical compositions thereof.

Several $N_1$-furoyl- and $N_1$-benzoyl-$N_2$-methyl-$N_2$-phenyl-1,3-diaminopropan-2-ol derivatives, which are not within the scope of the present invention, are known in the art and are specifically disclosed in the U.S. Pat. No. 3,998,809 and the German Offenlegungsschriften Nos. 22 21 558 and 23 14 993.

Several $N_1$-furoyl- and $N_1$-benzoyl-$N_2$-phenyl-1,3-diaminopropan-2-ol derivatives according to the present invention fall within the scope of the general formulae which are disclosed in the aforementioned patent and Offenlegungsschriften. Yet, these compounds are not specifically disclosed in these prior art publications. The German Offenlegungsschriften and the U.S. Pat. No. 3,998,809 disclose that the $N_1$-acyl-$N_2$-phenyl-1,3-diaminopropan-2-ol derivatives are valuable intermediates for the preparation of benzodiazepine- and benzodiazocine derivatives which are pharmacologically effective in influencing the central nervous system and which due to these properties are useful as tranquilizers, sedatives, or anticonvulsive agents. Yet, no independent pharmacological activity of these intermediates has been disclosed.

It is well known in the medical art that the etiology of ulcer-formation is very complex. Pharmaceuticals which so far have been used in the treatment of ulcers each influence only partial aspects of these multiple events. Therefore, only the limited therapeutical success could be obtained (see Blum, Schweiz. Med. Wochenschrift, 106 (1976) p. 1457).

According to Demling (see L. Demling, Klin. Gastroenterologie I, (1973), p. 202), the balance between the various aggressive and defensive factors which act on the mucous membrane is disturbed in the case of ulcer formation in the stomach and intestines. A therapeutical treatment therefore had to be directed towards redressing this balance.

The conventionally used therapeutic methods were directed towards reducing the aggressive agents (hydrochloric acid, pepsin).

Anticholinergic agents, as for example atropine, have not succeeded in ulcer-therapy, because of their side effects which occur already at low dosages. Antiacidic agents do not have a healing effect. Their therapeutical effect is limited only to a pain-reducing component which, with regard to ulcus duodeni, is doubted according to recent experiments (see Blum). Derivatives of glycyrrhetinic acid are known to have a therapeutic effect on ulcers. Yet, serious side-effects, such as aldosterone-like effects, causing a loss of potassium and sodium- and water-retention, strongly limit the possibility of a wider utilization of these derivatives. Psychopharmacological agents have not succeeded in the treatment of ulcers due to a lack of activity. Furthermore, their effects on the central nervous system, such as sedation and influence of motility, are undesirable in ambulatory treatment.

SUMMARY OF THE INVENTION

It is an object of the present invention to provide new pharmacologically active compounds and pharmaceutical compositions which are effective in the treatment of ulcers, in particular peptic ulcers, in larger mammals, in particular human beings. It is a further object of this invention to provide such compounds and compositions which exhibit a direct ulcer-inhibiting activity. It is a further object of the present invention to provide such compounds and compositions, which are low in side-effects and toxicity and exhibit a large therapeutic index.

It is a further object of the present invention to provide such compounds and compositions, which do not substantially influence the secretion in the stomach.

It is a further object of the present invention to provide such compounds and compositions which promote the redressing of the disturbed physiological balance at the mucous membrane and the regeneration of the impaired mucous membrane.

It is a further object of the present invention to provide a method of treatment of physiological disorders which are connected with the formation of ulcers, in particular a method for treatment of peptic ulcers.

It is a further object of the present invention to provide processes for preparing pharmacologically active compounds which are effective in preventing and/or healing ulcers.

In order to accomplish the foregoing objects according to the present invention, there are provided new compounds selected from the group of 1-acyl-amino-3-phenylaminopropan-2-ols, having the formula I

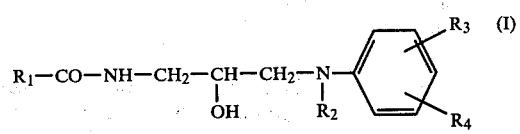

wherein $R_1$ represents alkyl containing 1 to about 20 carbon atoms, alkenyl containing 2 to about 7 carbon atoms, penta-1,3-dien-1-yl, cycloalkyl containing 3 to about 7 carbon atoms, lower alkyl substituted cycloalkyl containing 3 to about 7 carbon atoms in the cycloalkyl nucleus, cycloalkylmethyl containing 4 to about 8 carbon atoms, lower alkyl substituted cycloalkylmethyl containing 3 to about 7 carbon atoms in the cycloalkyl nucleus, cycloalkenyl containing 5 to about 7 carbon atoms, lower alkyl substituted cycloalkenyl containing 5 to about 7 carbon atoms in the cycloalkenyl nucleus, cycloalkenylmethyl containing 6 to about 8 carbon atoms, lower alkyl substituted cycloalkenylmethyl containing 5 to about 7 carbon atoms in the cycloalkyl nucleus, adamantyl, adamantylmethyl, benzyl, phenylethylenyl, 3,4-dimethoxybenzyl, 3,4-dimethoxyphenylethylenyl, pyridyl, 3,4-methylenedioxyphenyl, 3,4-ethylenedioxyphenyl, or 4-fluorophenyl, $R_2$ represents hydrogen, alkyl containing 1 to 3 carbon atoms, or methoxyethyl, and $R_3$ and $R_4$ are the same or different from each other and each represent hydrogen, fluorine, chlorine, bromine, iodine, alkyl containing 1 to 3 carbon atoms, or alkoxy containing 1 to 3 carbon atoms; or $R_1$ represents dimethoxyphenyl, 2-fluorophenyl, 2-trifluoromethylphenyl, or 2-furyl, $R_2$ represents hydrogen, alkyl containing 1 to 3 carbon atoms, or methoxyethyl, and $R_3$ and $R_4$ are the same or different from each other and each represent hydrogen, fluorine, chlorine, bromine, iodine, alkyl containing 1 to 3 carbon atoms, or alkoxy containing 1 to 3 carbon atoms; with exception of the compounds of the formula I, if $R_1$ represents 3,4-dimethoxyphenyl, 2-trifluoromethylphenyl, or 2-furyl, $R_2$ represents methyl, $R_3$ represents hydrogen, $R_4$ represents 4-chlorine; or $R_1$ represents 3,4-dimethoxyphenyl, $R_2$ represents methyl, $R_3$ and $R_4$ represents 3,4-dimethoxyphenyl; or $R_1$ represents 2-fluorophenyl, $R_2$ represents methyl, $R_3$ and $R_4$ each represent hydrogen; or $R_1$ represents 2-fluorophenyl, $R_2$ represents methyl or ethyl, $R_3$ represents hydrogen and $R_4$ represents 4-chlorine; and pharmaceutically acceptable acid addition salts thereof.

According to the present invention, there are further provided pharmaceutical compositions comprising an ulcus inhibiting effective amount of at least one compound selected from the group $N_1$-acyl-$N_2$-phenyl-1,3-diaminopropan-2-ol, having the formula I and pharmaceutically acceptable acid addition salts thereof, and a pharmaceutically acceptable diluent.

According to the present invention, there is further provided a method of treating disorders which are connected with the formation of ulcers, in particular peptic ulcers, in larger mammals, in particular human beings, which comprises the step of administering the above described pharmaceutical composition.

According to the present invention, there are further provided processes for preparing the compounds of formula I in good yields.

According to the present invention the 1-acylamino-3-phenylaminopropan-2-ols of formula I can be prepared by a process which comprises the steps of (a) reacting a 1,3-diaminopropan-2-ol having the formula II

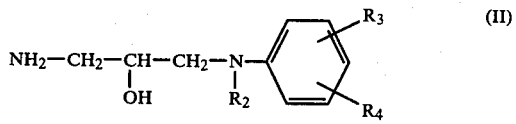

wherein $R_2$, $R_3$, and $R_4$ are as defined above with an acid derivative having the formula III

wherein $R_1$ is as defined above and X is halogen, lower alkoxy, or an

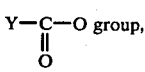

wherein Y represents lower alkoxy or the group $R_1$, whereby a reaction mixture containing 1-acylamino-3-phenylaminopropan-2-ol of formula I

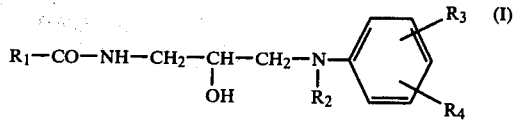

wherein $R_1$, $R_2$, $R_3$, and $R_4$ are as defined above is formed, and (b) recovering the compound of formula I from the reaction mixture.

According to the present invention the 1-acylamino-3-phenylaminopropan-2-ols of formula I can also be prepared by a process which comprises the steps of (a) reacting an acylamino compound having the formula IV $$R_1-CO-NH-CH_2-Z \qquad (IV)$$

wherein $R_1$ is as defined above and Z represents a

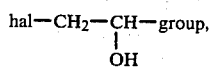

wherein hal is halogen, or Z is the

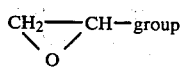

with an aniline compound having the formula V

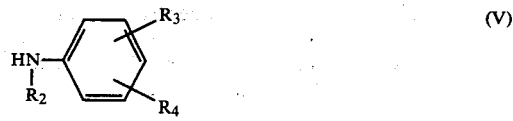

wherein $R_2$, $R_3$, and $R_4$ are as defined above at a reaction temperature of between about 15° and about 150° C., whereby a reaction mixture containing the 1acylamino-3-phenylaminopropan-2-ol of formula I

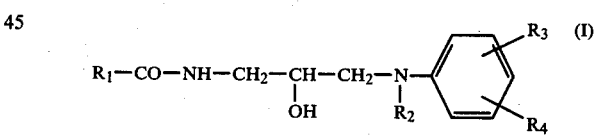

wherein $R_1$, $R_2$, $R_3$, and $R_4$ are as defined above is formed; and (b) recovering the compound formula I from the reaction mixture.

An 1-acylamino-3-phenylaminopropan-2-ol, having the formula Ia

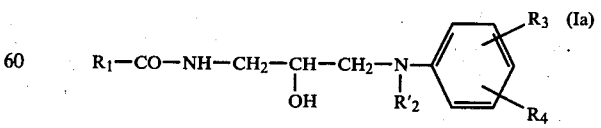

wherein $R_1$, $R_3$, and $R_4$ are as defined above and $R_2'$ is alkyl contaning 1–3 carbon atoms, or methoxyethyl can also be prepared according to the present invention by a process which comprises the step of alkylating a compound of formula Ib

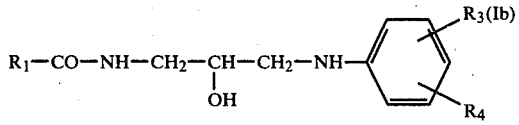

wherein $R_1$, $R_3$, and $R_4$ are as defined above.

Further objects, features, and advantages of the present invention will become apparent from the detailed description of the invention, which follows.

DETAILED DESCRIPTION OF THE INVENTION AND ITS PREFERRED EMBODIMENTS

It has been found that the compounds of formula I possess a therapeutic effect in the treatment of ulcers and disorders which are connected with formation of ulcers, without influencing the acid secretion in the stomach, or the central nervous system.

In the compounds of formula I, $R_2$ preferably represents methyl or hydrogen. Yet, it may also represent ethyl, propyl, or isopropyl or methoxyethyl.

In the compounds of formula I, $R_1$ preferably represents alkyl, cycloalkyl, or phenylalkyl, or phenylalkenyl, which may be substituted in the phenylnucleus or furyl or substituted phenyl.

If $R_1$ represents an alkyl group, this group may be straight or branched. Suitable alkyl groups, for example, are the following: methyl, ethyl, propyl, isopropyl, butyl, 2-butyl, 2-methylpropyl, tert.-butyl, pentyl, 2-pentyl, 2-methylbutyl, 3-methylbutyl, 3-pentyl, 1,1-dimethylpropyl, neopentyl, hexyl, 2-hexyl, 3-hexyl, 1,1-dimethylbutyl, heptyl, 2-heptyl, 3-heptyl, 4-heptyl, octyl, 3,4,4-trimethylphenyl, 1-methyl-1-ethylpentyl, nonyl, decyl, undecyl, dodecyl, tridecyl, tetradecyl, pentadecyl, hexadecyl, heptadecyl, octadecyl, nonadecyl or eicosyl. Preferred are the alkyl groups, containing 4 to 8 carbon atoms.

Suitable alkenyl groups are, for example, vinyl, 1-propen-1-yl, allyl, 3-buten-1-yl, 2,2-dimethylvinyl, 1,2-dimethylvinyl, 1-penten-1-yl, 1-hexen-1-yl, 4-hexen-1-yl, 1-hepten-1-yl, 5-hepten-1-yl. Preferred are alkenyl groups, containing about 5 carbon atoms and also 1,3-pentadien-1-yl, containing 2 double bonds.

Suitable cycloalkyl groups, which optionally may be connected to the carboxamide group by means of methylene are, for example, cyclopropyl, cyclobutyl, cyclopentyl, cyclohexyl, or cycloheptyl. These cycloalkyl- and cycloalkylmethylene groups may be substituted by methyl. Suitable examples are: 1-methylcyclopentyl, 1-methylcyclohexyl, and 1-methylcycloheptyl. Examples of suitable cycloalkenyl- and cycloalkenylmethyl-groups, containing one double bond are: 1-cyclopenten-1-yl, (1-cyclopenten-1-yl)methylene, (2-cyclopenten-1-yl)methylene, 1-cyclohexen-1-yl, 3-cyclohexen-1-yl, (1-cyclohexen-1-yl)methylene, (3-cyclohexen-1-yl)methylene, and 4-cyclohepten-1-yl.

The substituents $R_3$ and $R_4$ may be the same or different from each other. If $R_3$, and/or $R_4$ represent an alkyl group, this group preferably is in the 4-position and preferably is methyl, but may also be ethyl propyl or isopropyl. If $R_3$ and/or $R_4$ represent an alkoxy group, this group preferably is methoxy, but may also represent ethoxy, propoxy, or isopropoxy. Suitably, $R_3$ and/or $R_4$ represent hydrogen, halogen, methoxy, or methyl, whereby hydrogen, chlorine and fluorine are most preferred. Preferably one of $R_3$ and $R_4$ is hydrogen and the other represents a substitutent, preferably fluorine or chlorine, in the 4-position of the phenyl nucleus.

The new compounds of formula I and their acid addition salts exhibit an outstanding direct ulcer-inhibitory activity combined with a favorably large therapeutic index, without influencing the secretion in the stomach. Therefore, they lead to a redressing of the physiological balance at the mucous membrane which has been disturbed due to the illness. Furthermore, they are low in side-effects and toxicity.

Description of the pharmacological test methods

1. Acute toxicity

The acute 7-day-toxicity is determined after a single application per os in white NMRI-mice which had not been fed. The calculation of the $LD_{50}$ is carried out by probitanalysis by means of electronic data processing (see L. Cavalli-Sforza, Gustav Fischer-Verlag, Stuttgart (1964), Grundbergriffe der Biometrie, p. 153).

2. Effectiveness against indomethancine-induced ulcers in the rat (Modified test procedure according to U. Jahn and R. W. Adrian, Arzneimittel Forschung, (Drug Res.) 19, (1969), p. 36).

To at least 6 male rats, having a body-weight of from 170 to 220 g, dosages of the test compounds are administered orally in an amount of 0.5 ml of a suspension medium per 100 g animal body-weight. The animals of the blank control group receive the corresponding amount by volume of the suspension medium only. One hour after application of the test compounds, a dosage of 20 mg per kg of indomethacine contained in an amount of 0,5 ml of a suspension per 100 g animal body-weight, are orally applied to each animal for producing ulcers. 24 hours after the application of indomethacine, the animals are sacrificed.

The evaluation of the results is effected according to a modification of the method according to O. Muenchow, (Arzneim. Forsch. (Drug Res.) 4, (1954) pp. 341–344). The mean value and the standard deviation of the numbers of ulcers is calculated, and subsequently the inhibiting activity of the test compounds and a standard compound are calculated as percent inhibition compared with the blank control group.

3. Effect on the secretion in the stomach of narcotized rats (determination of the pH-value)

For evaluating the effect of the test compounds on the secretion in the stomach, a modification of the procedure according to M. N. Ghosh and H. O. Schild (Brit. J. Pharmacol. 13, (1958) p. 54) is used. The test is performed on narcotized (urethane narcosis) male rats, having a body-weight of 200-230 g. For this purpose N/4000-sodium hydroxide solution is perfused into the stomachs of rats at a rate of 1 ml per minute by means of a cardia- and polyorus-catheter. The pH value of the perfusate, which leaves the stomach by way of the pylorus catheter, is determined by means of a one-rod measuring system, and is continuously registered.

In order to perform a comparative control test, after a pre-run period of 20 minutes, 10 mg per kg of acetylcholine are applied intraperitoneally. The resulting comparative control value is defined as being 100.

After the starting value has been reached again, the test compound is applied intraduodeneously.

For evaluation, the surface-integral is calculated numerically with the aid of the rule of Simpson. The degree of inhibition of the secretion is calculated from the difference between the surfaces before and after the application of the test compound.

The following compounds of formula I have been tested according to the above described methods:

1. $N_1$-acetyl-$N_2$-methyl-$N_2$-(4-chlorophenyl)-1,3-diaminopropan-2-ol
2. $N_1$-hexanoyl-$N_2$-methyl-$N_2$-(4-fluorophenyl)-1,3-diaminopropan-2-ol
3. $N_1$-hexadecanoyl-$N_2$-methyl-$N_2$-(4-chlorophenyl)-1,3-diaminopropan-2-ol
4. $N_1$-cyclopropylcarbonyl-$N_2$-methyl-$N_2$-phenyl-1,3-diaminopropan-2-ol
5. $N_1$-cyclohexylcarbonyl-$N_2$-methyl-$N_2$-phenyl-1,3-diaminopropan-2-ol
6. $N_1$-cyclohexylcarbonyl-$N_2$-methyl-$N_2$-(4-fluorophenyl)-1,3-diaminopropan-2-ol
7. $N_1$-cyclohexylcarbonyl-$N_2$-propyl-$N_2$-phenyl-1,3-diaminopropan-2-ol
8. $N_1$-phenacetyl-$N_2$-methyl-$N_2$-(4-chlorophenyl)-1,3-diaminopropan-2-ol
9. $N_1$-cinnamoyl-$N_2$-methyl-$N_2$-(4-chlorophenyl)-1,3-diaminopropan-2-ol
10. $N_1$-(3,4-dimethoxycinnamoyl)-$N_2$-methyl-$N_2$-(4-chlorophenyl)-1,3-diaminopropan-2-ol
11. $N_1$-picolinoyl-$N_2$-methyl-$N_2$-(4-chlorophenyl)-1,3-diaminopropan-2-ol
12. $N_1$-furoyl-$N_2$-methyl-$N_2$-(3,4-dichlorophenyl)-1,3-diaminopropan-2-ol
13. $N_1$-furoyl-$N_2$-methoxyethyl-$N_2$-(4-chlorophenyl)-1,3-diaminopropan-2-ol
14. $N_1$-(3,4-dimethoxybenzoyl)-$N_2$-(2-chlorophenyl)-1,3-diaminopropan-2-ol
15. $N_1$-(3,4-dimethoxybenzoyl)-$N_2$-methyl-$N_2$-(4-fluorophenyl)-1,3-diaminopropan-2-ol
16. $N_1$-(3,4-dimethoxybenzoyl)-$N_2$-methyl-$N_2$-(3,4-dichlorophenyl)-1,3-diaminopropan-2-ol
17. $N_1$-(3,4-dimethoxybenzoyl)-$N_2$-propyl-$N_2$-(4-chlorophenyl)-1,3-diaminopropan-2-ol
18. $N_1$-(2-fluorobenzoyl)-$N_2$-methyl-$N_2$-(3,4-dichlorophenyl)-1,3-diaminopropan-2-ol
19. $N_1$-furoyl-$N_2$-methyl-$N_2$-(4-isopropylphenyl)-1,3-diaminopropan-2-ol.

The following have been used as standard control substances:
A. atropine sulfate
B. licorice extract.

The results are shown in Table I below. From the data in Table I it is apparent that the compound of formula I according to the present invention exhibit a good ulcer-inhibiting activity without inhibiting the secretion in the stomach.

TABLE I

| Compound No. | Toxicity $LD_{50}$ p.o. (mg/kg) | Inhibition of indomethacine induced ulcers | | Inhibition of secretion in the stomach | |
|---|---|---|---|---|---|
| | | dosage p.o. (mg/kg) | % inhibition | dosgae p.o. (mg/kg) | % inhibition |
| 1 | 2260 | 150 | 33 | 300 | 0 |
| 2 | 4320 | 150 | 44 | 300 | 0 |
| 3 | >6810 | 150 | 40 | 300 | 0 |
| 4 | >1470 | 147 | 36 | 300 | 0 |
| 5 | 3200 | 150 | 47 | 300 | 0 |
| 6 | >1470 | 150 | 40 | 300 | 0 |
| 7 | >1470 | 150 | 34 | 300 | 0 |
| 8 | 3860 | 75 | 26 | 300 | 0 |
| 9 | >6810 | 68 | 32 | 300 | 0 |
| 10 | >6810 | 75 | 32 | 300 | 0 |
| 11 | 3300 | 68 | 71 | 300 | 0 |
| 12 | >1470 | 75 | 29 | 300 | 0 |
| 13 | >1470 | 75 | 35 | 300 | 0 |
| 14 | >6700 | 75 | 33 | 300 | 0 |
| 15 | >6810 | 75 | 32 | 300 | 0 |
| 16 | >6810 | 75 | 38 | 300 | 0 |
| 17 | >6810 | 75 | 34 | 300 | 0 |
| 18 | >1470 | 75 | 33 | 300 | 0 |
| 19 | >1470 | 75 | 31 | 300 | 0 |
| A | 721 | 12 | 26 | 0.5 i.p.* | 100 |
| B | >10000 | 150 | 13 | 300 | 0 |

*At a low dosage already, atropine causes a strong inhibition of the secretion in the stomach, yet, at this point does not have a sufficiently strong effect on the ulcer. Higher dosages are not advisable due to the well known side-effects.

Due to their above mentioned pharmacological properties, the $N_1$-acyl-$N_2$-phenyl-1,3-diaminopropan-2-ols of formula I and their pharmaceutically acceptable acid addition salts, are useful in medical treatment, in particular in the treatment and prophylaxis of ulcers, in particular peptic ulcers, and physiological disorders which favor the formation of such ulcers.

According to a feature of the invention, there are provided pharmaceutical compositions containing at least one of the compounds of formula I or their pharmaceutically acceptable salts. The compositions may take the form of solid or liquid formulations for enteral, preferably oral, or for parenteral administration. Thus, the pharmaceutical formulations may be in solid form, e.g., in the form of capsules, tablets, coated tablets, or suppositories, or in liquid form, e.g., in the form of solutions, suspensions, or emulsions. These formulations may comprise conventional inorganic and/or organic inert pharmaceutical carriers and adjuvants, which are suitable for enteral and/or parenteral administration. Thus, the pharmaceutical diluents may comprise solids and/or liquid carrier materials, such as, e.g., lactose, starch, gum arabic, gelatin, vegetable oils, fats, polyethylene glycols, and the like. If desired, the pharmaceutical compositions according to the present invention, may further comprise conventional additives, such as preserving agents, stabilizing agents, moisturizers, emulsifying agents, or salts, which serve for regulating the osmotic pressure or as a buffer.

Suitable carrier materials and adjuvants are well known in the pharmaceutical art and are disclosed and/or recommended as adjuvants in the pharmaceutical and cosmetic art and related arts in the following publications, the disclosure of which is hereby incorporated by reference:

Ullmanns Encyclopedia der technischen Chemie, Vol. 4, (1953), p. 1; Journal of Pharmaceutical Sciences, Vol. 52, (1963), p. 918; Dr. H. P. Fiedler, Lexikon der Hilfsstoffe fuer Pharmazie, Kosmetik und angrenzende Gebiete, Cantor KG., Aulendorf i. Wuertt. 1971.

The pharmaceutical formulations according to the present invention are prepared in any conventional manner, e.g., by dissolving the pharmacologically active agents in at least a portion of liquid carrier materials or by thoroughly mixing the pharmacologically active agents with at least a portion of the solid carrier materials, adding the remaining adjuvants and/or carrier materials, and formulating the resulting mixtures into the desired dosage form by known pharmaceutical methods, e.g., tabletting, molding into suppositories, or filling into capsules. In addition to the $N_1$-acyl-$N_2$-phenyl-1,3-diaminopropan-2-ols of formula I, additional therapeutically active ingredients may optionally be included into the pharmaceutical formulations according to the present invention.

In the pharmaceutical compositions, according to the present invention, the amount of the pharmacologically active compound of formula I per single dosage unit may vary according to the type of the compound and the conditions to be treated. In pharmaceutical compositions for oral administration to adult humans, the amount of the compound of formula I per single dosage preferably is in the range of from about 50 to about 150 mg per single dosage unit.

The amount of compounds of formula I which suitably is applied for the treatment and prophylaxis of ulcers may of course vary according to the conditions to be treated and the mode of application. For oral application to adult persons, daily dosages of from about 150-450 mg are suitable.

According to the present invention, the compounds of formula I can be prepared by reacting an $N_1$-phenylamino-1,3-diaminopropan-2-ol of formula II with an acid derivative of formula III. This reaction suitably is carried out in an inert solvent. The reaction temperature preferably is between about $-10°$ C. and the boiling point of the reaction mixture, and the reaction may take place under normal pressure or under elevated pressure.

Preferably, the reaction is carried out in the presence of an acid-binding agent, for example, an inorganic base, such as an alkali carbonate or hydroxide, e.g., potassium carbonate, sodium carbonate, potassium hydroxide, or sodium hydroxide, or a tertiary organic amine, for example, triethylamine or pyridine. If an excess of such a tertiary organic amine is used, this amine simultaneously can serve as the inert solvent. Other suitable inert solvents are, e.g., methylene chloride, acetone, tetrahydrofurane, dioxane, benzene, toluene, or chlorobenzene. If a compound of formula III, wherein X represents lower alkoxy is used, it is advisable to perform the reaction in a closed container, whereby an excess of the ester of formula III may serve as a solvent. The reaction can be promoted by adding a metal alcoholate, e.g., aluminum isopropylate, as a catalyst.

Compounds of formula I, wherein $R_2$ represents hydrogen, that is compounds of formula Ib, can subsequently be alkylated in a conventional manner in order to obtain the corresponding compounds of formula Ia.

The methylation can be performed by conventional methods which are known from prior art literature, e.g., or the reaction with a lower aldehyde under reducing conditions by the method according to Eschweiler-Clarke (see H. Krauch, W. Kunz, Reactionen der organischen Chemie (1976), p. 131) or by alkylation with dialkylsulfate (see Houben-Weyl, XI/1 (1957), p. 207).

Pharmaceutically acceptable non-toxic acid addition salts of the compounds of formula I can be prepared in conventional manner by reacting the free base of formula I with an appropriate acid. Suitable acids are, e.g., mineral acids, such as sulfuric acid, hydrochloric acid, hydrobromic acid, or orthophosphoric acid, or organic acids, such as, e.g., malonic acid, succinic acid, fumaric acid, maleinic acid, p-toluenesulfonic acid, or cyclohexylaminosulfonic acid. The acid addition salts of the compounds of formula I can be pharmaceutically used in the same manner as the free base of formula I.

The starting materials of formula II may be prepared in a conventional manner, e.g., according to the method which is described by M. Chadwick et al. in J. Med. Chem. 9, p. 874 (1966).

According to the present invention the compounds of formula I may also be prepared by reacting an acylamino compound of formula IV with an aniline compound of formula V.

This reaction suitably is carried out in the presence of an additional solvent. The following are examples of suitable solvents: lower alkyl alcohols, such as methanol, ethanol, propanol, or isopropanol, ether, dioxane, tetrahydrofurane, benzene, toluene, xylene, sulfolane, dimethylformamide, dimethylsulfoxide, hexamethylphosphoric acid, and glacial acetic acid.

If a compound of formula IV is used, wherein Z represents the group

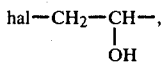

the halogen preferably is chlorine or bromine and the reaction is preferably carried out at a temperature of between about 15° and about 60° C. in the presence of an acid-binding agent, such as, e.g., potassium carbonate, sodium carbonate, sodium hydroxide, or potassium hydroxide. An excess of the aniline of formula V may serve as a solvent.

If in the compounds of formula IV Z represents an ethylenepoxy group, the reaction of this epoxide of formula IV with the aniline of formula V can suitably by carried out at the reflux temperature of the solvent. Yet, the reaction can also be carried out in the presence of a catalyst. Thus, e.g., the reaction can be carried out in the presence of glacial acetic acid.

Starting materials of formula IV, wherein Z represents a group

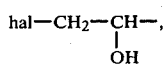

can, for example, be obtained by reacting a 2-phenyl-5-chloromethyloxazolidine derivative with an acid chloride of the formula $R_1$—COCl, wherein $R_1$ is as defined above, in a conventional method (H. E. Carter et al., J. Amer. Chem. Soc. 75, p. 2503 (1955), M. Bergmann et al., Chem. Ber. 54, p. 1645 (1921).

Starting materials of formula IV, wherein Z represents ethylenepoxy, can be prepared according to the methods disclosed in Houben-Weyl, Methoden der Org. Chemie, 6/3, p. 374 (1965), by treating the corresponding 1,2-halogenhydrines of formula IV with a strongly basic agent, e.g., pulverized sodium- or potassium hydroxide in an inert solvent, such as ether, dioxane, tetrahydrofurane, benzene, or toluene, at room temperature or elevated temperature. The resulting epoxides of formula IV can be further reacted in the process according to the present invention without any prior purification.

The following non-limiting examples are intended to further illustrate the present invention.

EXAMPLE 1

27.0 g of $N_1$-methyl-$N_1$-phenyl-1,3-diaminopropan-2-ol (IIa) are dissolved in 300 ml of chloroform. 16.5 g of triethylamine are added to the solution. Subsequently a solution of 15.4 g of acetic anhydride in 50 ml of chloroform are dropwise added to the reaction mixture at ambient temperature. After allowing the reaction mixture to stand at ambient temperature for 15 hours, water is added and thoroughly mixed therewith. The organic phase is separated, washed with water and dried over sodium sulfate. After filtering the solution and evaporating the solvent under vacuum, an oily residue is obtained and is crystallized from ethyl acetate/ether. 19.1 g of $N_1$-acetyl-$N_2$-methyl-$N_2$-phenyl-1,3-diaminopropan-2-ol, having a melting point of 73°–74° C. are obtained.

IR-Spectrum (KBr): 1637 cm$^{-1}$ (—CONH—).

EXAMPLE 2

The compound (IIa) is reacted with a corresponding amount of propionic acid anhydride, according to the procedure described in Example 1, whereby $N_1$-propionyl-$N_2$-methyl-$N_2$-phenyl-1,3-diaminopropan-2-ol, having a melting point of 75°–77° C., is obtained.

EXAMPLE 3

The compound (IIa) is reacted with the corresponding amount of butyric acid anhydride according to the procedure described in Example 1, whereby $N_1$-butyryl-$N_2$-methyl-$N_2$-phenyl-1,3-diaminopropan-2-ol, having a melting point of 55°–56° C., is obtained.

EXAMPLE 4

Instead of the compound (IIa), $N_1$-methyl-$N_1$-(4-fluorophenyl)-1,3-diaminopropan-2-ol (IIb) is reacted with the corresponding amount of butyric acid anhydride, according to the procedure described in Example 1, whereby $N_1$-butyryl-$N_2$-methyl-$N_2$-(4-fluorophenyl)-1,3-diaminopropan-2-ol, having a melting point of 59°–60° C., is obtained.

EXAMPLE 5

The compound (IIb) is reacted with a corresponding amount of isobutyric acid anhydride, according to the procedure described in Example 1, whereby $N_1$-isobutyryl-$N_2$-methyl-$N_2$-(4-fluorophenyl)-1,3-diaminopropan-2-ol, having a melting point of 110°–112° C., is obtained.

EXAMPLE 6

The compound (IIb) is reacted with a corresponding amount of valeric acid anhydride, according to the procedure described in Example 1, whereby $N_1$-valeryl-$N_2$-methyl-$N_2$-(4-fluorophenyl)-1,3-diaminopropan-2-ol, is obtained as an oil.

EXAMPLE 7

The compound (IIa) is reacted with a corresponding amount of hexanoic acid anhydride, according to the procedure described in Example 1, whereby $N_1$-hexanoyl-$N_2$-methyl-$N_2$-phenyl-1,3-diaminopropan-2-ol is obtained as an oil.

EXAMPLE 8

25.7 g of triethylamine are added to a solution of 50.0 g of $N_1$-methyl-$N_1$-(4-chlorophenyl)-1,3-diaminopropan-2-ol (IIc) in 500 ml of chloroform. Subsequently, 24.8 g of n-butyric acid chloride are added dropwise at ambient temperature. After 16 hours, water is added and thoroughly mixed with the reaction mixture. The organic phase is separated, washed with water and dried over sodium sulfate. After filtration and evaporation of the solvent under vacuum, an oily residue is obtained and is crystallized from ethyl acetate/petrolether. 45 g of $N_1$-butyryl-$N_2$-methyl-$N_2$-(4-chlorophenyl)-1,3-diaminopropan-2-ol, having a melting point of 72°–73° C., are obtained.

EXAMPLE 9

According to the procedure described in Example 8, $N_1$-methyl-$N_1$-phenyl-1,3-diaminopropan-2-ol (IIa) is reacted with the corresponding amount of 3,3-dimethylacrylic acid chloride and $N_1$-(3,3-dimethylacryloyl)-$N_2$-methyl-$N_2$-phenyl-1,3-diaminopropan-2-ol, having a melting point of 75°–77° C., is obtained.

EXAMPLE 10

According to the procedure described in Example 8, $N_1$-methyl-$N_1$-phenyl-1,3-diaminopropan-2-ol (IIa) is reacted with the corresponding amount of pivalic acid chloride and $N_1$-(2,2-dimethylpropionyl)-$N_2$-methyl-$N_2$-phenyl-1,3-diaminopropan-2-ol, having a melting point of 79°–80° C., is obtained.

EXAMPLE 11

According to the procedure described in Example 8, the compound (IIc) is reacted with the corresponding amount of isovaleric acid chloride and $N_1$-isovaleryl-$N_2$-methyl-$N_2$-(4-chlorophenyl)-1,3-diaminopropan-2-ol, having a melting point of 80°–82° C., is obtained.

EXAMPLE 12

According to the procedure described in Example 8, the compound (IIc) is reacted with the corresponding amount of hexanoic acid chloride and $N_1$-hexanoyl-$N_2$-methyl-$N_2$-(4-chlorophenyl)-1,3-diaminopropan-2-ol, having a melting point of 79°–80° C., is obtained.

IR-Spectrum (KBr): 1634 cm$^{-1}$ (—CONH—).

EXAMPLE 13

According to the procedure described in Example 8, $N_1$-methyl-$N_1$-(4-fluorophenyl)-1,3-diaminopropan-2-ol (IIb) is reacted with the corresponding amount of capronic acid chloride and $N_1$-hexanoyl-$N_2$-methyl-$N_2$-(4-fluorophenyl)-1,3-diaminopropan-2-ol, having a melting point of 46°–49° C., is obtained.

IR-Spectrum (KBr): 1642 cm$^{-1}$ (—CONH—).

EXAMPLE 14

The compound (IIb) is reacted with diethylacetic acid chloride according to the procedure described in Example 8 and $N_1$-diethylacetyl-$N_2$-methyl-$N_2$-(4-fluorophenyl)-1,3-diaminopropan-2-ol, having a melting point of 91°–92° C., is obtained.

EXAMPLE 15

The compound (IIc) is reacted with n-heptanoic acid chloride according to the procedure described in Example 8, and $N_1$-heptanoyl-$N_2$-methyl-$N_2$-(4-chlorophenyl)-1,3-diaminopropan-2-ol, having a melting point of 70°–71° C., is obtained.

EXAMPLE 16

21.5 g of the compound (IIc) are dissolved in 250 ml of benzene. 15 ml of pyridine are added and subsequently 16.3 g of caprylic acid chloride are added. After allowing the reaction mixture to stand for 15 hours, it is worked up according to Example 1. 20.4 g of $N_1$-capryloyl-$N_2$-methyl-$N_2$-(4-chlorophenyl)-1,3-diaminopropan-2-ol. having a melting point of 55°–56° C. after crystallization from hexane, are obtained.

EXAMPLE 17

The compound (IIb) is reacted with 2-ethylhexanoic acid chloride according to the procedure described in Example 8, whereby $N_1$-(2-ethylhexanoyl)-$N_2$-methyl-$N_2$-(4-fluorophenyl)-1,3-diaminopropan-2-ol, having a melting point of 73°–75° C., is obtained.

EXAMPLE 18

Under agitation, 17.7 g of pelargonic acid chloride are added dropwise to a solution of 21.5 g of $N_1$-methyl-$N_1$-(4-chlorophenyl)-1,3-diaminopropan-2-ol (IIc) in a mixture of 15 ml of pyridine and 250 ml of methylenechloride. The reaction mixture is allowed to stand at room temperature for 6 hours and then is heated to a temperature of 40° to 45° C., for 2 hours. Upon working up of the reaction mixture a raw oil is obtained. The latter is purified by filtration over aluminum oxide (activity degree II) using a mixture of toluene/chloroform as eluant. The resulting oil is crystallized from ether/hexane. 16.9 g of $N_1$-nonanoyl-$N_2$-methyl-$N_2$-(4-chlorophenyl)-1,3-diaminopropan-2-ol, having a melting point of 62°–64° C., are obtained.

EXAMPLE 19

The compound (IIc) is reacted with palmitic acidchloride according to the procedure described in Example 18, whereby $N_1$-hexadecanoyl-$N_2$-methyl-$N_2$-(4-chlorophenyl)-1,3-diaminopropan-2-ol, having a melting point of 78° C., is obtained.

EXAMPLE 20

The compound (IIc) is reacted with stearic acidchloride according to the procedure described in Example 18, whereby $N_1$-octadecanoyl-$N_2$-methyl-$N_2$-(4-chlorophenyl)-1,3-diaminopropan-2-ol, having a melting point of 52°–53° C., is obtained.

EXAMPLE 21

A mixture of 9 g of $N_1$-methyl-$N_1$-phenyl-1,3-diaminopropan-2-ol (IIa) and 150 ml of ethyl acetate is heated in an autoclave to a temperature of 130° C. for a period of 8 hours. Subsequently, the solvent is evaporated and the remaining raw oil is purified by means of chromatography on an aluminum oxide column (degree of activity II) using methylene chloride as an eluant. After crystallization from ethylacetate/ether, 6,8 g of $N_1$-acetyl-$N_2$-methyl-$N_2$-phenyl-1,3-diaminopropan-2-ol, having a melting point of 73°–74° C., are obtained.

EXAMPLE 22

In a modification of the procedure described in Example 21, a mixture of the compound (IIa) with 150 ml of ethyl acetate, to which 2 g of aluminum isopropylate are added, is heated to a temperature of 130° C. in an autoclave for a period of 8 hours. During the working up of the reaction mixture, the solvent is evaporated under vacuum, the raw oil is dissolved in 150 ml of ethanol and treated with 50 ml of a 10% aqueous sodium hydroxide solution under agitation. After a period of 1.5 hours, the ethanol is evaporated under vacuum. From the residue, 7.1 g of $N_1$-acetyl-$N_2$-methyl-$N_2$-phenyl-1,3-diaminopropan-2-ol, having a melting point of 73°–74° C., are obtained by means of crystallization from ethylacetate/ether.

EXAMPLE 23

The compound (IIa) is reacted with hepten-6-oic acid chloride, according to the procedure described in Example 8, whereby $N_1$-(6-heptenoyl)-$N_2$-methyl-$N_2$-phenyl-1,3-diaminopropan-2-ol, is obtained as an oil.

EXAMPLE 24

11.6 g of triethylamine and 11.9 g of chloroformic acid ethylester are added to a solution of 11.2 g of sorbic acid in 150 ml of chloroform at a temperature of between 0° and 5° C. After 30 minutes, the mixture is cooled to $-10°$ C. and a solution of 18 g of the compound (IIa) in 200 ml of chloroform is added. After standing at room temperature for 2 hours, the reaction mixture is worked up as described in Example 1. After crystallization from aceton/petrolether, 15 g of $N_1$-(2,4-hexadienoyl)-$N_2$-methyl-$N_2$-phenyl-1,3-diaminopropan-2-ol, having a melting point of 187°–189° C., are obtained.

EXAMPLE 25

The compound (IIa) is reacted with sorbic acid chloride according to the procedure described in Example 8, whereby $N_1$-(2,4-hexadienoyl)-$N_2$-methyl-$N_2$-phenyl-1,3-diaminopropan-2-ol, having a melting point of 187°–189° C., is obtained.

EXAMPLE 26

The compound (IIa) is reacted with the mixed anhydride of trans-hexen-3-oic acid according to the procedure described in Example 24, whereby $N_1$-(3-hexenoyl)-$N_2$-methyl-$N_2$-phenyl-1,3-diaminopropan-2-ol is obtained as an oil.

EXAMPLE 27

19 g of the compound (IIa) and 11.6 g of triethylamine are dissolved in 150 ml of chloroform and 11 g of cyclopropylcarboxylic acid chloride are added at room temperature. After the reaction mixture has been allowed to stand for 10 hours it is worked up as described in Example 1. 23 g of $N_1$-cyclopropylcarbonyl-$N_2$-methyl-$N_2$-phenyl-1,3-diaminopropan-2-ol, having a melting point of 86°–88° C., are obtained by crystallization from acetone/petrolether.

IR-Spectrum (KBr): 1645 $cm^{-1}$ (—CONH—).

EXAMPLE 28

The compound (IIa) is reacted with cyclobutylcarboxylic acid chloride according to the procedure described in Example 27, whereby $N_1$-cyclobutylcarbonyl-$N_2$-methyl-$N_2$-phenyl-1,3-diaminopropan-2-ol is obtained as an oil.

EXAMPLE 29

The compound (IIa) is reacted with cyclopentylcarboxylic acid chloride according to the procedure described in Example 27, whereby $N_1$-cyclopentylcarbonyl-$N_2$-methyl-$N_2$-phenyl-1,3-diaminopropan-2-ol, having a melting point of 88°–90° C., is obtained.

EXAMPLE 30

The compound (IIb) is reacted with cyclopentylcarboxylic acid chloride according to the procedure described in Example 27, whereby $N_1$-cyclopentylcarbonyl-$N_2$-methyl-$N_2$-(4-fluorophenyl)-1,3-diaminopropan-2-ol, having a melting point of 90°–92° C., is obtained.

EXAMPLE 31

The compound (IIc) is reacted with cyclopentylcarboxylic acid chloride according to the procedure described in Example 8, whereby $N_1$-cyclopentylcarbonyl-$N_2$-methyl-$N_2$-(4-chlorophenyl)-1,3-diaminopropan-2-ol, having a melting point of 94°–96° C., is obtained.

EXAMPLE 32

According to the procedure described in Example 27, 25 g of 3-anilino-1-aminopropan-2-ol are dissolved in 350 ml of chloroform, 16.6 g of triethylamine and then 22.1 g of cyclohexylcarboxylic acid chloride are added. 27 g of $N_1$-cyclohexylcarbonyl-$N_2$-phenyl-1,3-diaminopropan-2-ol, having a melting point of 149°–150° C. are obtained after crystallization from ethanol.

EXAMPLE 33

According to the procedure described in Example 27, 19 g of $N_1$-methyl-$N_1$-phenyl-1,3-diaminopropan-2-ol (IIa) are reacted with 15.5 g of cyclohexylcarboxylic acid chloride. After standing at room temperature for a period of 12 hours, the reaction product is worked up as is described in Example 1. 25.8 g of crystalline $N_1$-cyclohexylcarbonyl-$N_2$-methyl-$N_2$-phenyl-1,3-diaminopropan-2-ol, having a melting point of 83°–85° C., are obtained after crystallization from benzene/petrolether.
IR-Spectrum (KBr): 1642 cm$^{-1}$ (—CONH—).

EXAMPLE 34

In a modification of the procedure described in Example 33, 19 g of the compound (IIa) are dissolved in 150 ml of pyridine. 15.5 g of cyclohexylcarboxylic acid chloride are added dropwise into the solution, which has been cooled by means of ice. After a reaction period of 12 hours, the yield in isolated $N_1$-cyclohexylcarbonyl-$N_2$-methyl-$N_2$-phenyl-1,3-diaminopropan-2-ol, having a melting point of 83°–85° C., is 25 g.

EXAMPLE 35

In a modification of the procedure described in Example 33, 9 g of the compound (IIa) are dissolved in 200 ml of benzene and 10 ml of cyclohexylcarboxylic acid chloride are added. After the reaction mixture has been heated under reflux for a period of 4 hours, 50 ml of a 10% aqueous sodium hydroxide solution are added and the mixture is agitated at a temperature of 60° C. for a period of 1 hours. After the reaction mixture has been worked up as described in Example 1, 11 g of $N_1$-cyclohexylcarbonyl-$N_2$-methyl-$N_2$-phenyl-1,3-diaminopropan-2-ol, having a melting point of 83°–85° C., are obtained.

EXAMPLE 36

In a modification of the procedure described in Example 33, 12.8 g of cyclohexylcarboxylic acid are dissolved in 300 ml of chloroform. 11.1 g of triethylamine are added at a temperature of between 0°–5° C., and then 11.9 g of chloroformic acid ethyl ester are added. After 30 minutes the solution is cooled to −10° C. and a solution of 18 g of the compound (IIa) in 200 ml of chloroform is added. After allowing the reaction mixture to stand for 2 hours at a temperature of between 0°–5° C., the reaction mixture is worked up. The yield in $N_1$-cyclohexylcarbonyl-$N_2$-methyl-$N_2$-phenyl-1,3-diaminopropan-2-ol, having a melting point of 83°–85° C., is 20.4 g.

EXAMPLE 37

7.8 g of the $N_1$-cyclohexylcarbonyl-$N_2$-phenyl-1,3-diaminopropan-2-ol, which is obtained according to Example 32, are mixed with 54 ml of formic acid and 27 ml of 36% aqueous formaldehyde solution and the mixture is heated on a waterbath for a period of 3 hours. For working up, the mixture is poured on ice. Then the mixture is rendered alkaline by means of addition of diluted sodium hydroxide solution and is extracted with chloroform. After the chloroform extract has been worked up in the usual manner as described in Example 1, 6.2 g of $N_1$-cyclohexylcarbonyl-$N_2$-methyl-$N_2$-phenyl-1,3-diaminopropan-2-ol, having a melting point of 83°–85° C., are obtained.

EXAMPLE 38

2.3 g of the $N_1$-cyclohexylcarbonyl-$N_2$-phenyl-1,3-diaminopropan-2-ol, which has been obtained according to Example 32, are dissolved in 30 ml of dioxane, 2.5 g of sodium carbonate in 5 ml of water and 2.7 ml of dimethylsulfate are added and the mixture is agitated for 30 minutes at a temperature of 60° C. When 5 ml of 10% sodium hydroxide are added and the mixture is allowed to stand at the same temperature for another 10 minutes. Subsequently, the solvent is evaporated under vacuum and the product is isolated from chloroform as is described in Example 1. By means of crystallization, 1.6 g of $N_1$-cyclohexylcarbonyl-$N_2$-methyl-$N_2$-phenyl-1,3-diaminopropan-2-ol, having a melting point of 83°–85° C., are obtained.

EXAMPLE 39

$N_1$-(2-methylphenyl)-1,3-diaminopropan-2-ol is reacted with cyclohexylcarboxylic acid chloride, described in Example 32, whereby $N_1$-cyclohexylcarbonyl-$N_2$-(2methylphenyl)-1,3-diaminopropan-2-ol, having a melting point of 100°–103° C., is obtained.

EXAMPLE 40

$N_1$-(3-methylphenyl)-1,3-diaminopropan-2-ol is reacted with cyclohexylcarboxylic acid chloride, according to the procedure described in Example 32, whereby $N_1$-cyclohexylcarbonyl-$N_2$-(3-methylphenyl)-1,3-diaminopropan-2-ol, haing a melting point of 142°–145° C., is obtained.

EXAMPLE 41

$N_1$-(2-chlorophenyl)-1,3-diaminopropan-2-ol is reacted with cyclohexylcarboxylic acid chloride, according to the procedure described in Example 32, whereby $N_1$-cyclohexylcarbonyl-$N_2$-(2-chlorophenyl)-1,3-diaminopropan-2-ol, having a melting point of 87°–89° C., is obtained.

EXAMPLE 42

$N_1$-(4-bromophenyl)-1,3-diaminopropan-2-ol is reacted with cyclohexylcarboxylic acid chloride, according to the procedure described in Example 32, whereby $N_1$-cyclohexylcarbonyl-$N_2$-(4-bromophenyl)-1,3-diaminopropan-2-ol, having a melting point of 148°–150° C., is obtained.

EXAMPLE 43

$N_1$-(3-chloro-2-methylphenyl)-1,3-diaminopropan-2-ol is reacted with cyclohexylcarboxylic acid chloride, according to the procedure described in Example 32, whereby N$_1$-cyclohexylcarbonyl-N$_2$-(3-chloro-2-methylphenyl)-1,3-diaminpropan-2-ol, having a melting point of 124°–126° C., is obtained.

EXAMPLE 44

N$_1$-(2,6-dimethylphenyl)-1,3-diaminopropan-2-ol is reacted with cyclohexylcarboxylic acid chloride, according to the procedure described in Example 32, whereby N$_1$-cyclohexylcarbonyl-N$_2$-(2,6-dimethylphenyl)-1,3-diaminopropan-2-ol, having a melting point of 100°–101° C., is obtained.

EXAMPLE 45

According to the procedure described in Example 32, cyclohexylcarboxylic acid chloride is reacted with
(a) N$_1$-methyl-N$_1$-(4-methylphenyl)-1,3-diaminopropan-2-ol,
(b) N$_1$-methyl-N$_1$-(3-chlorophenyl)-1,3-diaminopropan-2-ol,
(c) N$_1$-methyl-N$_1$-(4-chlorophenyl)-1,3-diaminopropan-2-ol,
(d) N$_1$-methyl-N$_1$-(4-fluorophenyl)-1,3-diaminopropan-2-ol,
(e) N$_1$-methyl-N$_1$-(4-methoxyphenyl)-1,3-diaminopropan-2-ol,
(f) N$_1$-methyl-N$_1$-(3,4-dichlorophenyl)-1,3-diaminopropan-2-ol,
(g) N$_1$-methyl-N$_1$-(3,4-dimethoxyphenyl)-1,3-diaminopropan-2-ol,
(h) N$_1$-methyl-N$_1$-(4-isopropylphenyl)-1,3-diaminopropan-2-ol,
(i) N$_1$-ethyl-N$_1$-phenyl-1,3-diaminopropan-2-ol,
(k) N$_1$-propyl-N$_1$-phenyl-1,3-diaminopropan-2-ol,
(l) N$_1$-isopropyl-N$_1$-phenyl-1,3-diaminopropan-2-ol, or
(m) N$_1$-methoxyethyl-N$_1$-phenyl-1,3-diaminopropan-2-ol, in order to obtain the following compounds:
(a) N$_1$-cyclohexylcarbonyl-N$_2$-methyl-N$_2$-(4-methylphenyl)-1,3-diaminopropan-2-ol, melting point 110°–113° C.;
(b) N$_1$-cyclohexylcarbonyl-N$_2$-methyl-N$_2$-(3-chlorophenyl)-1,3-diaminopropan-2-ol, melting point 121°–123° C.;
(c) N$_1$-cyclohexylcarbonyl-N$_2$-methyl-N$_2$-(4-chlorophenyl)-1,3-diaminopropan-2-ol, melting point 112°–117° C.;
(d) N$_1$-cyclohexylcarbonyl-N$_2$-methyl-N$_2$-(4-fluorophenyl)-1,3-diaminopropan-2-ol, melting point 105°–106° C.;
(e) N$_1$-cyclohexylcarbonyl-N$_2$-methyl-N$_2$-(4-methoxyphenyl)-1,3-diaminopropan-2-ol, melting point 95°–98° C.;
(f) N$_1$-cyclohexylcarbonyl-N$_2$-methyl-N$_2$-(3,4-dichlorophenyl)-1,3-diaminopropan-2-ol, melting point 136°–138° C.;
(g) N$_1$-cyclohexylcarbonyl-N$_2$-methyl-N$_2$-(3,4-dimethoxyphenyl)-1,3-diaminopropan-2-ol, melting point 104°–105° C.;
(h) N$_1$-cyclohexylcarbonyl-N$_2$-methyl-N$_2$-(4-isopropylphenyl)-1,3-diaminopropan-2-ol, melting point 107°–108° C.;
(i) N$_1$-cyclohexylcarbonyl-N$_2$-ethyl-N$_2$-phenyl-1,3-diaminopropan-2-ol, melting point 87°–89° C.;
(k) N$_1$-cyclohexylcarbonyl-N$_2$-propyl-N$_2$-phenyl-1,3-diaminopropan-2-ol, melting point 84°–85° C.;
(l) N$_1$-cyclohexylcarbonyl-N$_2$-isopropyl-N$_2$-phenyl-1,3-diaminopropan-2-ol, melting point 80°–82° C.; or
(m) N$_1$-cyclohexylcarbonyl-N$_2$-methoxyethyl-N$_2$-phenyl-1,3-diaminopropan-2-ol, melting point 118°–120° C.

EXAMPLE 46

According to the reaction conditions described in Example 38, 3.8 g of N$_1$-cyclohexylcarbonyl-N$_2$-phenyl-1,3-diaminopropan-2-ol are dissolved in 30 ml of dioxane, 4.1 g of sodium bicarbonate in 6.9 ml of water and 6.0 ml of diethylsulfate are added and the mixture is heated to a temperature of 60° C. for a period of 30 minutes. The raw oil which is isolated as described in Example 38, is purified by preparative layer-chromatography (silica gel plates PF-254, manufacturer Merck, Darmstadt, using a mixture of chloroform/ethylacetate/ethanol 70/70/30 as eluant), and 2.1 g of N$_1$-cyclohexylcarbonyl-N$_2$-ethyl-N$_2$-phenyl-1,3-diaminopropan-2-ol, having a melting point of 87°–89° C., is obtained by crystallization from cyclohexane.

EXAMPLE 47

By reacting N$_1$-methyl-N$_1$-phenyl-1,3-diaminopropan-2-ol (IIa) with 1-methyl-cyclohexylcarboxylic acid chloride according to the procedure described in Example 32, N$_1$-(1-methylcyclohexylcarbonyl)-N$_2$-methyl-N$_2$-phenyl-1,3-diaminopropan-2-ol, having a melting point of 83°–85° C., is obtained.

EXAMPLE 48

The compound (IIa) is reacted with cyclohexylacetic acid chloride according to the procedure described in Example 32, whereby N$_1$-cyclohexylacetyl-N$_2$-methyl-N$_2$-phenyl-1,3-diaminopropan-2-ol, having a melting point of 100°–101° C., is obtained.

EXAMPLE 49

N$_1$-methyl-N$_1$-(3,4-dichlorophenyl)-1,3-diaminopropan-2-ol is reacted with cyclohexylacetic acid chloride according to the procedure described in Example 32, whereby N$_1$-cyclohexylacetyl-N$_2$-methyl-N$_2$-(3,4-dichlorophenyl)-1,3-diaminopropan-2-ol, having a melting point of 118°–121° C., is obtained.

EXAMPLE 50

N$_1$-methyl-N$_1$-phenyl-1,3-diaminopropan-2-ol (IIa) is reacted with (3-cyclohexen-1-yl)-carboxylic acid chloride according to the procedure described in Example 32, whereby N$_1$-(3-cyclohexen-1-yl-carbonyl)-N$_2$-methyl-N$_2$-phenyl-1,3-diaminopropan-2-ol, having a melting point of 87°–88° C., is obtained.

EXAMPLE 51

The compound (IIa) is reacted with cycloheptylcarboxylic acid chloride according to the procedure described in Example 32, whereby N$_1$-cycloheptylcarbonyl-N$_2$-methyl-N$_2$-phenyl-1,3-diaminopropan-2-ol, having a melting point of 89°–91° C., is obtained.

EXAMPLE 52

The compound (IIa) is reacted with 1-adamantylcarboxylic acid chloride according to the procedure described in Example 32, whereby N$_1$-(1-adamantylcarbonyl)-N$_2$-methyl-N$_2$-phenyl-1,3-diaminopropan-2-ol, having a melting point of 120°–122° C., is obtained.

EXAMPLE 53

The compound (IIa) is reacted with 1-adamantylacetic acid chloride according to the procedure described in Example 32, whereby $N_1$-(1-adamantylacetyl)-$N_2$-methyl-$N_2$-phenyl-1,3-diaminopropan-2-ol, having a melting point of 143°–144° C., is obtained.

EXAMPLE 54

The compound (IIc) is reacted with 1-adamantylacetic acid chloride according to the procedure described in Example 32. The reaction product is isolated and subsequently transformed into its hydrochloride. The resulting $N_1$-(1-adamantylacetyl)-$N_2$-methyl-$N_2$-(4-chlorophenyl)-1,3-diaminopropan-2-ol hydrochloride exhibits a melting point of between 166°–170° C.

EXAMPLE 55

According to the procedure described in Example 8, phenacetyl chloride is reacted with
(a) $N_1$-methyl-$N_1$-phenyl-1,3-diaminopropan-2-ol (IIa);
(b) $N_1$-methyl-$N_1$-(4-fluorophenyl)-1,3-diaminopropan-2-ol (IIb) or
(c) $N_1$-methyl-$N_1$-(4-chlorophenyl)-1,3-diaminopropan-2-ol (IIc)
and the following compounds are obtained:
(a) $N_1$-phenacetyl-$N_2$-methyl-$N_2$-phenyl-1,3-diaminopropan-2-ol, melting point 82°–84° C.;
(b) $N_1$-phenacetyl-$N_2$-methyl-$N_2$-(4-fluorophenyl)-1,3-diaminopropan-2-ol, melting point 84°–86° C.; or
(c) $N_1$-phenacetyl-$N_2$-methyl-$N_2$-(4-chlorophenyl)-1,3-diaminopropan-2-ol, melting point 88°–90° C.

EXAMPLE 56

In a modification of Example 55a, 3.6 g of $N_1$-methyl-$N_1$-phenyl-1,3-diaminopropan-2-ol (IIa) and 3.2 g of phenacetyl chloride are heated in 80 ml of benzene at reflux temperature for a period of 4 hours. Subsequently, 50 ml of 10% aqueous sodium hydroxide solution are added and the mixture is thoroughly mixed at a temperature of 60° C. for a period of 1 hour. After the reaction mixture has been worked up as described in Example 1 and the solvent has been evaporated from the dried solution, 3.7 g of crystalline $N_1$-phenacetyl-$N_2$-methyl-$N_2$-phenyl-1,3-diaminopropan-2-ol, having a melting point of 82°–84° C., are obtained after crystallization from aceton/ether.

EXAMPLE 57

In a modification of Example 55c, 7.5 g of phenylacetic acid methylester and 10.7 g of the compound (IIc) are heated in 100 ml of toluene at reflux temperature for a period of 6 hours. Water is added to the cooled solution and thoroughly mixed therewith. Thereby unreacted compounds (IIc) precipitates and is separated by filtration. The organic phase of the filtrate is worked up as described in Example 8, and after subsequent crystallization from aceton/petrolether, 4.0 g of $N_1$-phenacetyl-$N_2$-methyl-$N_2$-(4-chlorophenyl)-1,3-diaminopropan-2-ol, having a melting point of 88°–90° C., are obtained.

EXAMPLE 58

3,4-dimethoxyphenylacetic acid chloride is reacted with the compound (IIc) according to the procedure described in Example 8, whereby $N_1$-(3,4-dimethoxyphenylacetyl)-$N_2$-methyl-$N_2$-(4-chlorophenyl)-1,3-diaminopropan-2-ol is obtained. Melting point of the p-toluenesulfonate is 170°–172° C.

EXAMPLE 59

According to the procedure described in Example 55, cinnamoyl chloride is reacted with the compounds (IIa), (IIb), or (IIc) and the following compounds are obtained:
(a) $N_1$-cinnamoyl-$N_2$-methyl-$N_2$-phenyl-1,3-diaminopropan-2-ol, melting point 121°–123° C.;
(b) $N_1$-cinnamoyl-$N_2$-methyl-$N_2$-(4-fluorophenyl)-1,3-diaminopropan-2-ol, melting point 116°–118° C.; or
(c) $N_1$-cinnamoyl-$N_2$-methyl-$N_2$-(4-chlorophenyl)-1,3-diaminopropan-2-ol, melting point 114°–115° C.

EXAMPLE 60

According to the procedure described in Example 8, $N_1$-(3,4-dimethoxycinnamoyl)-$N_2$-methyl-$N_2$-(4-chlorophenyl)-1,3-diaminopropan-2-ol, having a melting point of between 119°–123° C., is obtained by reacting 3,4-dimethoxycinnamoyl chloride with the compound (IIc).

EXAMPLE 61

A solution of 15.3 g of nicotinoyl chloride in 50 ml of chloroform is added dropwise to a solution of 23.0 g of $N_1$-methyl-$N_1$-(4-chlorophenyl)-1,3-diaminopropan-2-ol (IIc) and 12.1 ml of triethylamine in 200 ml of chloroform under agitation at room temperature. After 16 hours water is added to the reaction mixture and is thoroughly mixed therewith. Subsequently, the organic phase is separated, washed with water and dried over sodium sulfate. After filtration and evaporation of the solvent under vacuum, an oily residue is obtained which crystallizes from benzene. 26.5 g of $N_1$-nicotinyl-$N_2$-methyl-$N_2$-(4-chlorophenyl)-1,3-diaminopropan-2-ol, having a melting point of 112°–114° C., are obtained.

EXAMPLE 62

The compound (IIc) is reacted with isonicotinoyl chloride according to the procedure described in Example 55. The resulting amide is isolated and transformed into its hydrochloride. $N_1$-isonicotinoyl-$N_2$-methyl-$N_2$-(4-chlorophenyl)-1,3-diaminopropan-2-ol hydrochloride, having a melting point of 180°–182° C., is obtained.

EXAMPLE 63

At a temperature of between 0°–5° C., 12 ml of chloroformic acid ethylester are added to a solution of 13.5 g of picolinic acid and 15 ml of triethylamine in 250 ml of chloroform. After 30 minutes, the reaction mixture is cooled to −10° C. and a solution of 21.5 g of $N_1$-methyl-$N_1$-(4-chlorophenyl)-1,3-diaminopropan-2-ol (IIc) in 200 ml of dimethylformamide is added. The temperature is allowed to re-rise to between 0°–5° C. After 2 hours the solvent is evaporated under vacuum, the residue is dissolved in chloroform and the resulting solution is worked up. The isolated raw oil is crystallized from benzene and 22 g of $N_1$-picolinoyl-$N_2$-methyl-$N_2$-(4-chlorophenyl)-1,3-diaminopropan-2-ol, having a melting point of 106°–107° C., are obtained.

EXAMPLE 64

According to the procedure described in Example 8, furoyl chloride is reacted with
(a) $N_1$-methyl-$N_1$-(2-fluorophenyl)-1,3-diaminopropan-2-ol,
(b) $N_1$-methyl-$N_1$-(3-fluorophenyl)-1,3-diaminopropan-2-ol,
(c) $N_1$-methyl-$N_1$-(3,4-dimethoxyphenyl)-1,3-diaminopropan-2-ol,
(d) $N_1$-methyl-$N_1$-(3,4-dichlorophenyl)-1,3-diaminopropan-2-ol, or (e) $N_1$-(2-methoxyethyl)-$N_1$-(4-chlorophenyl)-1,3-diaminopropan-2-ol, and the following compounds are obtained:
(a) $N_1$-furoyl-$N_2$-methyl-$N_2$-(2-fluorophenyl)-1,3-diaminopropan-2-ol, as an oil;
(b) $N_1$-furoyl-$N_2$-methyl-$N_2$-(3-fluorophenyl)-1,3-diaminopropan-2-ol, melting point 86°–88° C.;
(c) $N_1$-furoyl-$N_2$-methyl-$N_2$-(3,4-dimethoxyphenyl)-1,3-diaminopropan-2-ol, melting point 81°–83° C.;
(d) $N_1$-furoyl-$N_2$-methyl-$N_2$-(3,4-dichlorophenyl)-1,3-diaminopropan-2-ol, melting point 73°–77° C.; or
(e) $N_1$-furoyl-$N_2$-(2-methoxyethyl)-$N_2$-(4-chlorophenyl)-1,3-diaminopropan-2-ol, melting point 106°–108° C.

EXAMPLE 65

The solution of 40.0 g of 3,4-dimethoxybenzoyl chloride in 50 ml of chloroform is added dropwise to a solution of 36.0 g of $N_1$-methyl-$N_1$-phenyl-1,3-diaminopropan-2-ol and 22 g of triethylamine in 400 ml of chloroform at room temperature. After 16 hours, water is added to the reaction mixture, subsequently the organic phase is separated, washed with water, dried over sodium sulfate, and filtered. The residue which is obtained after evaporating the solvent under vacuum crystallizes from aceton/petrolether. 56.5 g of $N_1$-(3,4-dimethoxybenzoyl)-$N_2$-methyl-$N_2$-phenyl-1,3-diaminopropan-2-ol, having a melting point of 141°–143° C., are obtained.

EXAMPLE 66

In a modification of the reaction conditions described in Example 65, a mixture of 5 g of dimethoxybenzoyl chloride in 100 ml of dioxane, 4.5 g of $N_1$-methyl-$N_1$-phenyl-1,3-diaminopropan-2-ol and 4 g of potash is agitated for 12 hours. Then the mixture is filtered, the solvent is evaporated from the filtrate under vacuum and the remaining residue is heated in a mixture of 50 ml of methanol and 15 ml of 10% sodium hydroxide solution to a temperature of 60° C. for a period of 1 hour. The solvent is evaporated under vacuum, when the mixture is extracted with chloroform and the product is isolated from the chloroform-extract, as is described in Example 65. After crystallization from aceton/ether, 5.8 g of crystalline $N_1$-(3,4-dimethoxybenzoyl)-$N_2$-methyl-$N_2$-phenyl-1,3-diaminopropan-2-ol, having a melting point of 141°–142° C., are obtained.

EXAMPLE 67

In modifying the reaction conditions of Example 65, 6.7 g of chloroformic acid ethylester are added to a solution of 10.2 g of veratric acid in a mixture of 6.2 g of triethylamine and 300 ml of chloroform at a temperature of between 0°–5° C. After 30 minutes the reaction mixture is cooled to −10° C. and a solution of 10.1 g of $N_1$-methyl-$N_1$-phenyl-1,3-diaminopropan-2-ol in 150 ml of chloroform is added. The temperature is allowed to re-rise to 0°–5° C. After a period of 2 hours, the solution is worked up as is described in Example 65. By crystallizing the isolated raw oils, 12.9 g of $N_1$-(3,4-dimethoxybenzoyl)-$N_2$-methyl-$N_2$-phenyl-1,3-diaminopropan-2-ol, having a melting point of 141°–143° C., are obtained.

EXAMPLE 68

According to the procedure described in Examples 65 to 67, the $N_1$-acyl-$N_2$-phenyl-1,3-diaminopropan-2-ol compounds, which are listed in Table 1 below, can be prepared by reacting the corresponding N-phenyl-1,3-diaminopropan-2-ol compounds with the corresponding dimethoxy-, 3,4-methylenedioxy-, or 3,4-ethylenedioxybenzoic acid derivatives.

TABLE 1

| | Mp °C. |
|---|---|
| $N_1$—(2,3-dimethoxybenzoyl)-$N_2$—methyl-$N_2$—(4-chlorophenyl)-1,3-diaminopropan-2-ol | 96–97 |
| $N_1$—(2,4-dimethoxybenzoyl)-$N_2$—methyl-$N_2$—(4-chlorophenyl)-1,3-diaminopropan-2-ol | 132–134 |
| $N_1$—(3,5-dimethoxybenzoyl)-$N_2$—methyl-$N_2$—(4-chlorophenyl)-1,3-diaminopropan-2-ol | 128–130 |
| $N_1$—(2,6-dimethoxybenzoyl)-$N_2$—methyl-$N_2$—(4-chlorophenyl)-1,3-diaminopropan-2-ol | 140–142 |
| $N_1$—(3,4-dimethoxybenzoyl)-$N_2$—phenyl-1,3-diaminopropan-2-ol | Oil |
| $N_1$—(3,4-dimethoxybenzoyl)-$N_2$—(2-chlorophenyl)-1,3-diaminopropan-2-ol | 114–116 |
| $N_1$—(3,4-dimethoxybenzoyl)-$N_2$—(4-chlorophenyl)-1,3-diaminopropan-2-ol | 168–170 |
| $N_1$—(3,4-dimethoxybenzoyl)-$N_2$—(4-fluorophenyl)-1,3-diaminopropan-2-ol | Oil |
| $N_1$—(3,4-dimethoxybenzoyl)-$N_2$—(4-bromophenyl)-1,3-diaminopropan-2-ol | 166–168 |
| $N_1$—(3,4-dimethoxybenzoyl)-$N_2$—(4-methoxyphenyl)-1,3-diaminopropan-2-ol | 125–127 |
| $N_1$—(3,4-dimethoxybenzoyl)-$N_2$—(2-methylphenyl)-1,3-diaminopropan-2-ol | 122–125 |
| $N_1$—(3,4-dimethoxybenzoyl)-$N_2$—(3-methylphenyl)-1,3-diaminopropan-2-ol | 96–100 |
| $N_1$—(3,4-dimethoxybenzoyl)-$N_2$—(3-chloro-2-methyl-phenyl)-1,3-diaminopropan-2-ol hydrochloride | 158–163 |
| $N_1$—dimethoxybenzoyl)-$N_2$—(2,6-dimethyl-phenyl)-1,3-diaminopropan-2-ol | 99–101 |
| $N_1$—(3,4-dimethoxybenzoyl)-$N_2$—methyl-$N_2$—(3-chlorophenyl)-1,3-diaminopropan-2-ol | 155–159 |
| $N_1$—(3,4-dimethoxybenzoyl)-$N_2$—methyl-$N_2$—(4-bromophenyl)-1,3-diaminopropan-2-ol | 102–105 |
| $N_1$—(3,4-dimethoxybenzoyl)-$N_2$—methyl-$N_2$—(4-fluorophenyl)-1,3-diaminopropan-2-ol | 132–134 |
| $N_1$—(3,4-dimethoxybenzoyl)-$N_2$—methyl-$N_2$—(4-methylphenyl)-1,3-diaminopropan-2-ol | 104–108 |
| $N_1$—(3,4-dimethoxybenzoyl)-$N_2$—methyl-$N_2$—(4-isopropylphenyl)-1,3-diaminopropan-2-ol | 107–108 |
| $N_1$—(3,4-dimethoxybenzoyl)-$N_2$—methyl-$N_2$—(3,4-dichlorophenyl)-1,3-diaminopropan-2-ol | 138–142 |
| $N_1$—(3,4-dimethoxybenzoyl)-$N_2$—ethyl-$N_2$—phenyl-1,3-diaminopropan-2-ol | 143–145 |
| $N_1$—(3,4-dimethoxybenzoyl)-$N_2$—propyl-$N_2$—(4-chlorophenyl)-1,3-diaminopropan-2-ol | 126–128 |
| $N_1$—(3,4-dimethoxybenzoyl)-$N_2$—isopropyl-$N_2$—phenyl-1,3-diaminopropan-2-ol | 103–104 |
| $N_1$—(3,4-methylenedioxybenzoyl)-$N_2$—(4-chlorophenyl)-1,3-diaminopropan-2-ol | 158–160 |
| $N_1$—(3,4-methylenedioxybenzoyl)-$N_2$—methyl-$N_2$—(4-chlorophenyl)-1,3-diaminopropan-2-ol | 140–143 |
| $N_1$—(3,4-ethylenedioxybenzoyl)-$N_2$—methyl-$N_2$—(4-chlorophenyl)-1,3-diaminopropan-2-ol | 186–187 |

EXAMPLE 69

According to the procedure described in Example 65, a solution of 39.6 g of $N_1$-methyl-$N_1$-(4-fluorophenyl)-1,3-diaminopropan-2-ol in a mixture of 35.0 ml of chloroform and 23.0 g of triethylamine is reacted with 33.0 g of 2-fluorobenzoyl chloride for a period of 14 hours. After appropriately working up the reaction mixture, 44.1 g of crystalline $N_1$-(2-fluorobenzoyl)-$N_2$-methyl-$N_2$-(4-fluorophenyl)-1,3-diaminopropan-2-ol, having a melting point of 95°–96° C., are obtained after crystallization from toluene.

EXAMPLE 70

A mixture of 3.6 g of $N_1$-methyl-$N_1$-phenyl-1,3-diaminopropan-2-ol and 4.0 g of 2-fluorobenzoyl chloride in 100 ml of benzene is heated to reflux temperature for a period of 6 hours. Subsequently, 20 ml of 10% aqueous sodium hydroxide solution are added and the reaction mixture is thoroughly mixed at a temperature of 60° C. for a period of 1.5 hours. Then the phases are separated from each other and the organic phase is worked up as is described in Example 65. After the raw product has been purified by chromatography over aluminum oxide (degree of activity I) using a mixture of chloroform/toluene as an eluant, the product is crystallized from a mixture of isopropanol/cyclohexane and 3.8 g of $N_1$-(2-fluorobenzoyl)-$N_2$-methyl-$N_2$-phenyl-1,3-diaminopropan-2-ol, having a melting point of 91°–92° C., are obtained.

EXAMPLE 71

According to the procedure described in Examples 69 and 70, the $N_1$-acyl-$N_2$-phenyl-1,3-diaminopropan-2-ol compounds, which are listed in Table 2, are prepared from the corresponding N-phenyl-1,3-diaminopropan-2-ol compounds and the corresponding 2-fluoro-, 4-fluoro-, or 2-trifluoromethylbenzoic acid derivatives.

TABLE 2

| | Mp. °C. |
|---|---|
| $N_1$—(2-fluorobenzoyl)-$N_2$—phenyl-1,3-diaminopropan-2-ol | Oil |
| $N_1$—(2-fluorobenzoyl)-$N_2$—(2-chlorophenyl)-1,3-diaminopropan-2-ol | 79–81 |
| $N_1$—(2-fluorobenzoyl)-$N_2$—(4-chlorophenyl)-1,3-diaminopropan-2-ol | 156–157 |
| $N_1$—(2-fluorobenzoyl)-$N_2$—(4-bromophenyl)-1,3-diaminopropan-2-ol | 151–152 |
| $N_1$—(2-fluorobenzoyl)-$N_2$—(2-methylphenyl)-1,3-diaminopropan-2-ol | 90–94 |
| $N_1$—(2-fluorobenzoyl)-$N_2$—(3-methylphenyl)-1,3-diaminopropan-2-ol | 74–76 |
| $N_1$—(2-fluorobenzoyl)-$N_2$—methyl-$N_2$—(4-isopropylphenyl)-1,3-diaminopropan-2-ol | 81–83 |
| $N_1$—(2-fluorobenzoyl)-$N_2$—methyl-$N_2$—(3,4-dimethoxyphenyl)-1,3-diaminopropan-2-ol | 96–97 |
| $N_1$—(2-fluorobenzoyl)-$N_2$—methyl-$N_2$—(3,4-dichlorophenyl)-1,3-diaminopropan-2-ol | 100 |
| $N_1$—(2-fluorobenzoyl)-$N_2$—ethyl-$N_2$—phenyl-1,3-diaminopropan-2-ol | 84–85 |
| $N_1$—(2-fluorobenzoyl)-$N_2$—propyl-$N_2$—phenyl-1,3-diaminopropan-2-ol | 63–64 |
| $N_1$—(2-fluorobenzoyl)-$N_2$—isopropyl-$N_2$—phenyl-1,3-diaminopropan-2-ol | 101–102 |
| $N_1$—(4-fluorobenzoyl)-$N_2$—methyl-$N_2$—(4-isopropylphenyl)-1,3-diaminopropan-2-ol | 142–143 |
| $N_1$—(4-fluorobenzoyl)-$N_2$—ethyl-$N_2$—phenyl-1,3-diaminopropan-2-ol | 94–96 |
| $N_1$—(4-fluorobenzoyl)-$N_2$—propyl-$N_2$—phenyl-1,3-diaminopropan-2-ol | 96–97 |
| $N_1$—(2-trifluoromethylbenzoyl)-$N_2$—methyl-$N_2$—phenyl-1,3-diaminopropan-2-ol | 96–98 |
| $N_1$—(2-trifluoromethylbenzoyl)-$N_2$—methyl-$N_2$—(4-fluorophenyl)-1,3-diaminopropan-2-ol | 88–89 |

EXAMPLE 72

According to the procedure described in Example 65, a solution of 25.9 g of $N_1$-methyl-$N_1$-(4-bromophenyl)-1,3-diaminopropan-2-ol in 200 ml of chloroform is reacted with 13.1 g of furan-2-carboxylic acid chloride in the presence of 11.1 g of triethylamine at room temperature for a period of 14 hours. After working up the reaction mixture and crystallizing the raw product from isopropanol, 21 g of crystalline $N_1$-furoyl-$N_2$-methyl-$N_2$-(4-bromophenyl)-1,3-diaminopropan-2-ol, having a melting point of 106°–107° C., are obtained.

EXAMPLE 73

According to the procedure described in Example 67, 11.2 g of furan-2-carboxylic acid are dissolved in a mixture of 300 ml of chloroform and 11.1 g of triethylamine, and 11.9 g of chloroformic acid ethylester are added to this solution at a temperature of 0°–5° C. After 30 minutes, the reaction mixture is cooled to −10° C. and a solution of 25.9 g of $N_1$-methyl-$N_2$-(4-bromophenyl)-1,3-diaminopropan-2-ol in 200 ml of chloroform is added. Subsequently, the temperature is again allowed to rise to 0°–5° C. After a reaction period of 2 hours, the solution is worked up as is described in Example 65. After crystallization from isopropanol, 23.2 g of $N_1$-furoyl-$N_2$-methyl-$N_2$-(4-bromophenyl)-1,3-diaminopropan-2-ol, having a melting point of 105°–107° C., are obtained.

EXAMPLE 74

According to the procedures described in Examples 72 and 73, the $N_1$-furoyl-$N_2$-phenyl-1,3-diaminopropan-2-ol compounds which are listed in Table 3, are prepared from the corresponding N-phenyl-1,3-diaminopropan-2-ol- or $N_1$-alkyl-$N_1$-phenyl-1,3-diaminopropan-2-ol compounds with furancarboxylic acid derivatives.

TABLE 3

| | Mp. °C. |
|---|---|
| $N_1$—furoyl-$N_2$—(4-bromophenyl)-1,3-diaminopropan-2-ol | 132–134 |
| $N_1$—furoyl-$N_2$—(4-chlorophenyl)-1,3-diaminopropan-2-ol | 125–127 |
| $N_1$—furoyl-$N_2$—(4-methoxyphenyl)-1,3-diaminopropan-2-ol | 113–116 |
| $N_1$—furoyl-$N_2$—methyl-$N_2$—(4-fluorophenyl)-1,3-diaminopropan-2-ol | Oil |
| $N_1$—furoyl-$N_2$—methyl-$N_2$—(4-methylphenyl)-1,3-diaminopropan-2-ol | 87–88 |
| $N_1$—furoyl-$N_2$—methyl-$N_2$—(4-isopropylphenyl)-1,3-diaminopropan-2-ol | 112–113 |
| $N_1$—furoyl-$N_2$—ethyl-$N_2$—phenyl-1,3-diaminopropan-2-ol | 81–82 |
| $N_1$—furoyl-$N_2$—propyl-$N_2$—(4-chlorophenyl)-1,3-diaminopropan-2-ol | 104–105 |
| $N_1$—furoyl-$N_2$—isopropyl-$N_2$—phenyl-1,3-diaminopropan-2-ol | 89–90 |

EXAMPLE 75

15.7 g of acetylchloride are added dropwise to a solution of 39.5 g of 2-phenyl-5-chloromethyloxazolidine in a mixture of 150 ml of chloroform and 16 ml of pyridine at a temperature of −40° C. under agitation. The solution is allowed to warm up to room temperature. After a reaction period of 14 hours, 100 ml of concentrated hydrochloric acid are added. After thoroughly mixing, the aqueous phase is separated and diluted with water to twice its volume and then is saturated with sodium chloride. By extracting the aqueous phase with methylene chloride, drying the methylene-chloride-extract and evaporating the solvent, 19.7 g of N-acetyl-3-chloro-1-aminopropan-2-ol is obtained as an oil which can be used in the following reaction without any purification.

15 g of N-acetyl-3-chloro-1-aminopropan-2-ol are added to a mixture of 6.1 g of pulverized potassium hydroxide in 200 ml of dioxane. 14 g of 4-chloroaniline are added and the mixture is agitated at room temperature for a period of 14 hours. The mixture is then filtered and the solvent is evaporated from the filtrate under vacuum. The residue is mixed with a small amount of ethanol. After adding ether, 8 g of $N_1$-acetyl-$N_2$-(4-chlorophenyl)-1,3-diaminopropan-2-ol, having a melting point of 123°–124° C., are crystallized.

EXAMPLE 76

According to a modification of Example 75, 4.7 g N-acetyl-3-chloro-1-aminopropan-2-ol and 4.0 g 4-chloroaniline are dissolved in 50 ml of isopropanol, 10 ml of 30% aqueous sodium hydroxide solution are added and the mixture is agitated at room temperature for a period of 14 hours. Then the reaction mixture is diluted with toluene, and the organic phase is separated, washed with water, dried over sodium sulfate, and filtered. After evaporating the solvent under vacuum, an oily residue is obtained. This residue is treated with ether, in order to remove unreacted 4-chloroaniline. As has been described in Example 75, 3.0 g of $N_1$-acetyl-$N_2$-(4-chlorophenyl)-1,3-diaminopropan-2-ol, having a melting point of 123°–124° C., are crystallized from ethanol/ether.

EXAMPLE 77

A mixture of 6.8 g of $N_1$-acetyl-$N_2$-(4-chlorophenyl)-1,3-diaminopropan-2-ol, which is obtained according to Example 75, 54 ml of formic acid and 27 ml of 36% aqueous formaldehyde solutions are heated on a water-bath for a period of 3 hours. For working up the mixture is brought onto ice. Then it is rendered alkaline by adding diluted sodium hydroxide solution, and is extracted with chloroform. The organic phase is separated, washed with water, dried over sodium sulfate, and filtered. After evaporating the solvent under vacuum, an oily residue is obtained which crystallizes from ethyl acetate/ether. 4.8 g of $N_1$-acetyl-$N_2$-methyl-$N_2$-(4-chlorophenyl)-1,3-diaminopropan-2-ol, having a melting point of 85°–86° C., are obtained.

EXAMPLE 78

A mixture of 3.0 g of $N_1$-acetyl-$N_2$-(4-chlorophenyl)-1,3-diaminopropan-2-ol in 45 ml of dioxane, 3.7 g of sodium bicarbonate in 7.5 ml of water, and 4.1 ml of dimethylsulfate is stirred for 30 minutes at a temperature of 60° C. Then 10 ml of 10% sodium hydroxide solution are added and the mixture is kept at the same temperature for another 10 minutes. Subsequently, the solvent is evaporated under vacuum and chloroform is added to the residue. After working up according to the procedure described in Example 75, 2.0 g of $N_1$-acetyl-$N_2$-methyl-$N_2$-(4-chlorophenyl)-1,3-diaminopropan-2-ol, having a melting point of 85°–86° C., are obtained.

EXAMPLE 79

19.8 g of 2-phenyl-5-chloromethyloxazolidine are reacted with 14.7 g of cyclohexylcarbonyl chloride in a mixture of 8 ml of pyridine and 100 ml of chloroform, according to the procedure described in Example 75. After crystallization of the raw product from ether/petrolether, 14.0 g of N-cyclohexylcarbonyl-3-chloro-1-aminopropan-2-ol, having a melting point of 90°–91° C., are obtained.

4.4 g of the amide, which has been obtained in this manner, are reacted with 2.2 g of aniline in 50 ml of dioxane under addition of 1.3 g of potassium hydroxide, according to the procedure described in Example 75. 3.0 g of crystalline $N_1$-cyclohexylcarbonyl-$N_2$-phenyl-1,3-diaminopropan-2-ol, having a melting point of 149°–150° C., are obtained after crystallization from ethanol.

EXAMPLE 80

A mixture of 1 g N-methylaniline and 2.0 g of N-cyclohexylcarbonyl-3-chloro-1-aminopropan-2-ol is heated to a temperature of 130° C. for a period of 2 hours. After cooling the reaction mixture, it is dissolved in chloroform, and washed with diluted aqueous sodium hydroxide solution. After working up, according to the procedure described in Example 75, a raw oil is obtained. The raw oil is purified by chromatography over a column of aluminum oxide (degree of activity II), using a mixture of toluene/methylenechloride as eluant. After crystallization from ethyl acetate, 1.4 g of $N_1$-cyclohexylcarbonyl-$N_2$-methyl-$N_2$-phenyl-1,3-diaminopropan-2-ol, having a melting point of 83°–85° C., are obtained.

EXAMPLE 81

In a modification of Example 80, 2.2 g of N-cyclohexylcarbonyl-3-chloro-1-aminopropan-2-ol are reacted with 1.3 g of N-methylaniline in 50 ml of dioxane under addition of 0.7 g of potassium hydroxide according to the procedure discribed in Example 79. 2.3 g of $N_1$-cyclohexylcarbonyl-$N_2$-methyl-$N_2$-phenyl-1,3-diaminopropan-2-ol, having a melting point of 83°–85° C., are obtained by crystallization from benzene/petrolether.

EXAMPLE 82

N-cyclohexylcarbonyl-3-chloro-1-aminopropan-2-ol are reacted with 3-chloro-2-methylaniline, according to the procedure described in Example 75, whereby $N_1$-cyclohexylcarbonyl-$N_2$-(3-chloro-2-methylphenyl)-1,3-diaminopropan-2-ol, having a melting point of 122°–123° C., is obtained.

EXAMPLE 83

A mixture of 6.0 g of N-cyclohexylcarbonyl-3-chloro-1-aminopropan-2-ol and 1.8 g of pulverized potassium hydroxide in 80 ml of ether is agitated at room temperature for a period of 18 hours. When sodium sulfate is added, the mixture filtered and the solvent is partially evaporated under vacuum. After cooling, 4.5 g of N-cyclohexylcarbonyl-2,3-epoxy-1-aminopropane, having a melting point of 78°–80° C., crystallizes. A mixture of 2.5 g of the thus obtained epoxide, 1.5 g of N-methylaniline and 0.8 g of glacial acetic acid is heated to a temperature of 60° C. for a period of 5 hours. Subsequently, the reaction mixture is dissolved in chloroform, the solution is washed with aqueous sodium hydroxide solution and is worked up as described in Example 77. 2.6 g of $N_1$-cyclohexylcarbonyl-$N_2$-methyl-$N_2$-phenyl-1,3-diaminopropan-2-ol, having a melting point of 83°–85° C., are obtained after crystallization from ethylacetate.

EXAMPLE 84

In a modification of Example 83, a mixture of 1.8 g of N-cyclohexylcarbonyl-2,3-epoxy-1-aminopropane and 1.1 g of N-methylaniline in 50 ml of isopropanol are heated to reflux temperature for a period of 6 hours. According to the procedure described in the foregoing example, the solvent is evaporated under vacuum and the residue is crystallized from ethylacetate. 1.6 g of crystalline $N_1$-cyclohexylcarbonyl-$N_2$-methyl-$N_2$-phenyl-1,3-diaminopropan-2-ol, having a melting point of 83°–85° C., are obtained.

EXAMPLE 85

According to the procedure described in Example 75, 2-phenyl-5-chloromethyloxazoline is reacted with 3,4-dimethoxyphenylacetyl chloride, whereby N-(3,4-dimethoxyphenylacetyl)-3-chloro-1-aminopropan-2-ol, having a melting point of 128°–130° C. is obtained. In a benzene/tetrahydrofurane mixture the foregoing compound is further reacted according to the procedure described in Example 83, whereby N-(3,4-dimethoxyphenylacetyl)-2,3-epoxy-1-aminopropane, having a melting point of 71°–74° C., is obtained.

A mixture of 5.2 g of the foregoing epoxy-compound, 1.2 g of acetic acid and 2.9 g of N-methyl-4-chloroaniline is heated to a temperature of 60° C. for a period of 5 hours. The reaction mixture is worked up as is described in Example 84, whereby an oil is obtained. This raw oil is reacted with p-toluenesulfonic acid and the resulting p-toluenesulfonic acid salt is treated with petrolether and crystallized from acetone. 6.0 g of $N_1$-(3,4-dimethoxyphenylacetyl)-$N_2$-methyl-$N_2$-(4-chlorophenyl)-1,3-diaminopropan-2-ol p-toluenesulfonate, having a melting point of 170°–172° C., are obtained.

EXAMPLE 86

According to the procedure described in Example 75, 9.1 g of N-furoyl-3-chloro-1-aminopropan-2-ol (melting point 73°–74° C.) are reacted with 2.6 g of potassium hydroxide in 130 ml of tetrahydrofurane, whereby 7.0 g of N-furoyl-2,3-epoxy-1-aminopropane are obtained as a raw oil. Without any further purification, this raw oil is reacted with 4.6 g of 3-fluoroaniline and 2.7 g of acetic acid. After working up the reaction mixture, 4.6 g of $N_1$-furoyl-$N_2$-(3-fluorophenyl)-1,3-diaminopropan-2-ol are obtained as an oil.

EXAMPLE 87

According to the procedure described in Example 77, a mixture of 4.5 g of $N_1$-furoyl-$N_2$-(3-fluorophenyl)-1,3-diaminopropan-2-ol, 31 ml of formic acid and 15.5 ml of 36% aqueous formaldehyde solution is heated on a waterbath for 3 hours and then is worked up as described in Example 77. After crystallization from isopropanol/ether, 2.2 g of $N_1$-furoyl-$N_2$-methyl-$N_2$-(3-fluorophenyl)-1,3-diaminopropan-2-ol, having a melting point of 86°–88° C., are obtained.

Examples 85 to 87 show that all new 1-acylamino-3-phenylaminopropan-2-ol compounds of formula I can also be obtained according to process (b) of the present invention.

EXAMPLE 88

A solution of 15.2 g of 3,4-dimethoxybenzoyl chloride in 40 ml of chloroform is added dropwise to a solution of 15.0 g 2-phenyl-5-chloromethyloxazolidine in a mixture of 200 ml of chloroform and 6 ml of pyridine at a temperture of −40° C. under agitation. This solution is then heated to room temperature. After a reaction period of 14 hours, 20 ml of concentrated hydrochloric acid are added, the phases are thoroughly mixed for a period of 10 minutes and then are separated. The separated aqueous phase is diluted with water to twice its volume and then is saturated with sodium chloride and extracted with chloroform. After drying the chloroform-extract and evaporating the solvent, 15.0 g of N-(3,4-dimethoxybenzoyl)-3-chloro-1-aminopropan-2-ol is obtained as an oil which can be further reacted without any purification. After crystallization from ethanol/toluene the compound exhibits a melting point of 104°–106° C.

8.2 of the foregoing compound and 4.0 g of 4-chloroaniline are added to a mixture of 1.8 g of finely pulverized potassium hydroxide in 160 ml of dioxane. After agitating the mixture for 14 hours at room temperature, the mixture is filtered and the solvent is evaporated from the filtrate under vacuum. The remaining residue is taken up in chloroform and is washed with water. After drying the chloroform phase and evaporating the solvent, 5.1 g of $N_1$-(3,4-dimethoxybenzoyl)-$N_2$-(4-chlorophenyl)-1,3-diaminopropan-2-ol is obtained as an oily residue which crystallizes from acetone. Melting point 168°–170° C.

EXAMPLE 89

A mixture of 3.5 g of N-(3,4-dimethoxybenzoyl)-3-chloro-1-aminopropan-2-ol and 0.8 g of finely pulverized potassium hydroxide in 250 ml of benzene is agitated at room temperature for a period of 16 hours. The reaction mixture is filtered and the solvent is evaporated from the filtrate. After crystallization from toluene, 2.5 g of N-(3,4-dimethoxybenzoyl)-2,3-epoxy-1-aminopropane, having a melting point of 108°–111° C., are obtained.

A mixture of 2.4 g of the above described epoxide, 1.9 g of 4-bromo-N-methylaniline and 0.7 g of acetic acid is heated to a temperature of 60° C. for a period of 6 hours. Subsequently, the reaction mixture is dissolved in chloroform, the chloroform phase is washed with water, dried over sodium sulfate and filtered. After evaporating the solvent, 2.6 g of $N_1$-(3,4-dimethoxybenzoyl)-$N_2$-methyl-$N_2$-(4-bromophenyl)-1,3-diaminopropan-2-ol are obtained. The oily compound is crystallized from acetone/petrolether and thereafter exhibits a melting point of 103°–105° C.

EXAMPLE 90

A mixture of 4.2 g of N-(3-chloro-2-hydroxypropyl)-3,4-dimethoxybenzamide, 75 ml of dioxane, 3.0 g of 4-bromoaniline, and 1.0 g of pulverized potassium hydroxide is agitated for 6 hours at a temperature of 30°–40° C. Then the mixture is filtered, the solvent is evaporated under vacuum, and the remaining raw oil is filtered over aluminum oxide (degree of activity II) using a mixture of chloroform/ethylacetate as a solvent. 2.7 g of $N_1$-(3,4-dimethoxybenzoyl)-$N_2$-(4-bromophenyl)-1,3-diaminopropan-2-ol are crystallized from acetone/petrolether. Melting point 166°–168° C.

EXAMPLE 91

A mixture of 4.1 g of $N_1$-3,4-dimethoxybenzoyl)-$N_2$-(4-bromophenyl)-1,3-diaminopropan-2-ol, 19 ml of formic acid and 10 ml of 36% aqueous formaldehyde solution are heated on a waterbath for 3 hours. Subsequently, the reaction mixture is poured onto ice, is rendered alkaline by addition of diluted sodium hydroxide solution and is extracted with chloroform. The compound is isolated from the chloroform extract. 3.3 g of $N_1$-(3,4-dimethoxybenzoyl)-$N_2$-methyl-$N_2$-(4-bromophenyl)-1,3-diaminopropan-2-ol are obtained which after crystallization from ethylacetate exhibit a melting point of 103°–195° C.

EXAMPLE 92

3.4 g of $N_1$-(3,4-dimethoxybenzoyl)-$N_2$-(4-bromophenyl)-1,3-diaminopropan-2-ol are dissolved in 60 ml of dioxane. 2.5 g of sodium bicarbonate in 5 ml of water are added. Then 2.7 ml of dimethylsulfate are added and the mixture is heated to a temperature of 60°–70° C. for a period of 30 minutes. Subsequently, 10 ml of 15% sodium hydroxide solution are stirred into the mixture, the solvent is evaporated under vacuum, the residue is extracted with chloroform and the compound is isolated from the chloroform phase. 2.0 g of $N_1$-(3,4-dimethoxybenzoyl)-$N_2$-methyl-$N_2$-(4-bromophenyl)-1,3-diaminopropan-2-ol, having a melting point of 103°–105° C., are obtained.

EXAMPLE 93

According to the procedure described in Example 88, 5.6 of N-(3-chloro-2-hydroxypropyl)-3,4-dimethoxybenzamide are reacted with 2 g of aniline and 1.2 g of potassium hydroxide in 350 ml of benzene. From the reaction mixture $N_1$-(3,4-dimethoxybenzoyl)-$N_2$-phenyl-1,3-diaminopropan-2-ol is isolated as a raw oil. 3.1 g of this raw oil in 30 ml of dioxane are reacted with 4.1 ml of diethylsulfate and 2.7 g of sodium bicarbonate in 5.6 ml of water, according to the procedure described in Example 92. 1.3 g of $N_1$-(3,4-dimethoxybenzoyl)-$N_2$-ethyl-$N_2$-phenyl-1,3-diaminopropan-2-ol are obtained. The compound crystallizes from ethylacetate and exhibits a melting point of 143° to 145° C.

EXAMPLE 94

A mixture of 2.4 g of N-(2,3-epoxypropyl)-3,4-dimethoxybenzamide and 1.2 g of N-methylaniline in 30 ml of toluene are heated to reflux temperature for a period of 5 hours. Subsequently, the reaction mixture is evaporated to dryness under vacuum and the remaining residue is purified by filtration over aluminum oxide (degree of activity II) using chloroform/toluene as an eluant. After crystallization from acetone/petrolether, 2.2 g of crystalline $N_1$-(3,4-dimethoxybenzoyl)-$N_2$-methyl-$N_2$-phenyl-1,3-diaminopropan-2-ol are obtained. Melting point 141°–143° C.

EXAMPLE 95

According to the procedure described in Example 89, 14.5 g of N-(3,4-methylenedioxybenzoyl)-3-chloro-1-aminopropan-2-ol, having a melting point of 128°–130° C., are reacted with 3.5 g of potassium hydroxide in 600 ml of benzene. Subsequently, the reaction mixture is dried over sodium sulfate, filtered and partially evaporated under vacuum. From the concentrated solution, 10.5 g of N-(3,4-methylenedioxybenzoyl)-2,3-epoxy-1-aminopropane, having a melting point of 117°–119° C., are obtained.

A mixture of 2.2 g of the above described epoxide, 1.5 g of 4-chloro-N-methylaniline and 1 ml of acetic acid are heated to a temperature of 60° C. for a period of 6 hours. After working up of the reaction mixture according to Example 89, 2.0 g of $N_1$-(3,4-methylenedioxybenzoyl)-$N_2$-methyl-$N_2$-(4-chlorophenyl)-1,3-diaminopropan-2-ol, having a melting point of 140°–143° C. after crystallization from methylene chloride/ether are obtained.

EXAMPLE 96

According to the procedure described in Example 89, N-(2,3-epoxypropyl)-3,4-methylenedioxybenzamide and 4-chloroaniline are reacted, whereby $N_1$-(3,4-methylenedioxybenzoyl)-$N_2$-(4-chlorophenyl)-1,3-diaminopropan-2-ol, having a melting point of 158°–160° C. are obtained.

EXAMPLE 97

According to the procedure described in Example 91, 9.8 g of $N_1$-(3,4-methylenedioxybenzoyl)-$N_2$-(4-chlorophenyl)-1,3-diaminopropan-2-ol are reacted with 54 ml of formic acid and 27 ml of 36% formaldehyde solution. The resulting compound crystallizes from methylene chloride/ether. 1 g of $N_1$-(3,4-methylenedioxybenzoyl)-$N_2$-methyl-$N_2$-(4-chlorophenyl)-1,3-diaminopropan-2-ol, having a melting point of 140°–143° C., are obtained.

EXAMPLE 98

According to the procedures described in Examples 88 to 97, the $N_1$-acyl-$N_2$-phenyl-1,3-diaminopropan-2-ol- or $N_1$-acyl-$N_2$-alkyl-$N_2$-phenyl-1,3-diaminopropan-2-ol compounds, which are listed in Table 4 below, are prepared from the corresponding N-dimethoxybenzoyl-, N-(3,4-methylenedioxybenzoyl)-, or N-(3,4-ethylenedioxybenzoyl)-3-chloro-1-aminopropan-2-ol compounds, whereby the resulting $N_1$-acyl-$N_2$-phenyl-1,3-diaminopropan-2-ol compounds may further be alkylated to obtain the corresponding $N_1$-acyl-$N_2$-alkyl-$N_2$-phenyl-1,3-diaminopropan-2-ol compounds.

TABLE 4

| | Mp. °C. |
|---|---|
| $N_1$—(2,3-dimethoxybenzoyl)-$N_2$—methyl-$N_2$—(4-chlorophenyl)-1,3-diaminopropan-2-ol | 96–97 |
| $N_1$—(2,4-dimethoxybenzoyl)-$N_2$—methyl-$N_2$—(4-chlorophenyl)-1,3-diaminopropan-2-ol | 132–134 |
| $N_1$—(3,5-dimethoxybenzoyl)-$N_2$—methyl-$N_2$—(4-chlorophenyl)-1,3-diaminopropan-2-ol | 128–130 |
| $N_1$—(3,4-dimethoxybenzoyl)-$N_2$—methyl-$N_2$—(4-fluorophenyl)-1,3-diaminopropan-2-ol | 132–134 |
| $N_1$—(3,4-dimethoxybenzoyl)-$N_2$—methyl-$N_2$—(4-methylphenyl)-1,3-diaminopropan-2-ol | 104–108 |
| $N_1$—(3,4-dimethoxybenzoyl)-$N_2$—methyl-$N_2$—(4-isopropylphenyl)-1,3-diaminopropan-2-ol | 107–108 |
| $N_1$—(3,4-dimethoxybenzoyl)-$N_2$—methyl-$N_2$—(3,4-dichlorophenyl)-1,3-diaminopropan-2-ol | 138–142 |
| $N_1$—(3,4-dimethoxybenzoyl)-$N_2$—propyl-$N_2$—(4-chlorophenyl)-1,3-diaminopropan-2-ol | 126–128 |
| $N_1$—(3,4-dimethoxybenzoyl)-$N_2$—isopropyl-$N_2$—phenyl-1,3-diaminopropan-2-ol | 103–104 |
| $N_1$—(3,4-ethylenedioxybenzoyl)-$N_2$—methyl-$N_2$—(4-chlorophenyl)-1,3-diaminopropan-2-ol | 186–187 |
| $N_1$—(2,6-dimethoxybenzoyl)-$N_2$—methyl-$N_2$—(4-chlorophenyl)-1,3-diaminopropan-2-ol | 140–142 |
| $N_1$—(3,4-dimethoxybenzoyl)-$N_2$—(2-chlorophenyl)-1,3-diaminopropan-2-ol | 114–116 |
| $N_1$—(3,4-dimethoxybenzoyl)-$N_2$—(4-fluorophenyl)-1,3-diaminopropan-2-ol | Oil |
| $N_1$—(3,4-dimethoxybenzoyl)-$N_2$—(4-methoxyphenyl)-1,3-diaminopropan-2-ol | 125–127 |
| $N_1$—(3,4-dimethoxybenzoyl)-$N_2$—(2-methylphenyl)-1,3-diaminopropan-2-ol | 122–125 |
| $N_1$—(3,4-dimethoxybenzoyl)-$N_2$—(3-methylphenyl)-1,3-diaminopropan-2-ol | 96–100 |
| $N_1$—(3,4-dimethoxybenzoyl)-$N_2$—(3-chloro-2-methylphenyl)-1,3-diaminopropan-2-ol hydrochloride | 158–163 |
| $N_1$—(3,4-dimethoxybenzoyl)-$N_2$—(2,6-dimethylphenyl)-1,3-diaminopropan-2-ol | 99–101 |
| $N_1$—(3,4-dimethoxybenzoyl)-$N_2$—methyl-(3-chlorophenyl)-1,3-diaminopropan-2-ol | 155–159 |

EXAMPLE 99

2-chloromethyl-5-phenyloxazolidine is reacted with 2-fluorobenzoyl chloride according to the procedure described in Example 88, whereby N-(3-chloro-2-hydroxypropyl)-2-fluorobenzamide, having a melting point of 77°–78° C., is obtained. According to the procedure described in Example 88, 3.9 g of the foregoing amide compound are reacted with 2.0 g of N-methylaniline and 1.0 g potassium hydroxide in 50 ml of dioxane. The reaction mixture is worked up and the resulting product is crystallized from isopropanol/cyclohexane. 1.9 g of $N_1$-(2-fluorobenzoyl)-$N_2$-methyl-$N_2$-phenyl-1,3-diaminopropan-2-ol, having a melting point of 91°–92° C., are obtained.

EXAMPLE 100

According to the procedure described in Example 89, 2.3 g of N-(3-chloro-2-hydroxypropyl)-2-fluorobenzamide are reacted with potassium hydroxide to N-(2,3-epoxypropyl)-2-fluorobenzamide. In a modification of the procedure described in Example 89, without any further purification, the resulting raw oil is heated with 1.1 g of N-methylaniline in 50 ml of toluene to reflux temperature for 6 hours. After evaporation of the solvent, 1.6 g of $N_1$-(2-fluorobenzoyl)-$N_2$-methyl-$N_2$-phenyl-1,3-diaminopropan-2-ol, having a melting point of 91°–92° C., are crystallized from isopropanol/cyclohexane.

EXAMPLE 101

According to the procedure described in Example 99, N-(3-chloro-2-hydroxypropyl)-2-fluorobenzamide are reacted with aniline, whereby $N_1$-(2-fluorobenzoyl)-$N_2$-phenyl-1,3-diaminopropan-2-ol is obtained as an oil.

EXAMPLE 102

A mixture of 2.9 g of $N_1$-(2-fluorobenzoyl)-$N_2$-phenyl-1,3-diaminopropan-2-ol in 25 ml of dioxane, 3.0 g of sodium bicarbonate in 6 ml of water and 4.4 ml of diethylsulfate is heated to a temperature of 60° C. for a period of 30 minutes. After the reaction mixture has been worked up as is described in Example 93, 1.5 g of $N_1$-(2-fluorobenzoyl)-$N_2$-ethyl-$N_2$-phenyl-1,3-diaminopropan-2-ol, having a melting point of 84°–85° C., are obtained after crystallization from isopropanol/cyclohexane.

EXAMPLE 103

According to the procedures described in the Examples 99 to 102, the $N_1$-acyl-$N_2$-phenyl-1,3-diaminopropan-2-ol- or $N_1$-acyl-$N_2$-alkyl-$N_2$-phenyl-1,3-diaminopropan-2-ol compounds, which are listed in Table V, are prepared from the corresponding N-(2-fluorobenzoyl)-, N-(4-fluorobenzoyl)-, or N-(2-trifluoromethylbenzoyl)-3-chloro-1-aminopropan-2-ol compounds, whereby the resulting $N_1$-acyl-$N_2$-phenyl-1,3-diaminopropan-2-ol compounds can be alkylated into the corresponding $N_1$-acyl-$N_2$-alkyl-$N_2$-phenyl-1,3-diaminopropan-2-ol compounds.

TABLE 5

|  | Mp. °C. |
|---|---|
| $N_1$—(2-fluorobenzoyl)-$N_2$—(2-chlorophenyl)-1,3-diaminopropan-2-ol | 79–81 |
| $N_1$—(2-fluorobenzoyl)-$N_2$—(4-chlorophenyl)-1,3-diaminopropan-2-ol | 156–157 |
| $N_1$—(2-fluorobenzoyl)-$N_2$—(4-bromophenyl)-1,3-diaminopropan-2-ol | 151–152 |
| $N_1$—(2-fluorobenzoyl)-$N_2$—(2-methylphenyl)-1,3-diaminopropan-2-ol | 90–94 |
| $N_1$—(2-fluorobenzoyl)-$N_2$—(3-methylphenyl)-1,3-diaminopropan-2-ol | 74–76 |
| $N_1$—(2-fluorobenzoyl)-$N_2$—methyl-$N_2$—(4-fluorophenyl)-1,3-diaminopropan-2-ol | 95–96 |
| $N_1$—(2-fluorobenzoyl)-$N_2$—methyl-$N_2$—(4-isopropylphenyl)-1,3-diaminopropan-2-ol | 81–83 |
| $N_1$—(2-fluorobenzoyl)-$N_2$—methyl-$N_2$—(3,4-dimethoxyphenyl)-1,3-diaminopropan-2-ol | 96–97 |
| $N_1$—(2-fluorobenzoyl)-$N_2$—methyl-$N_2$—(3,4-dichlorophenyl)-1,3-diaminopropan-2-ol | 100 |

TABLE 5-continued

|  | Mp. °C. |
|---|---|
| $N_1$—(2-fluorobenzoyl)-$N_2$—propyl-$N_2$—phenyl-1,3-diaminopropan-2-ol | 63–64 |
| $N_1$—(2-fluorobenzoyl)-$N_2$—isopropyl-$N_2$—phenyl-1,3-diaminopropan-2-ol | 101–102 |
| $N_1$—(4-fluorobenzoyl)-$N_2$—methyl-$N_2$—(4-isopropylphenyl)-1,3-diaminopropan-2-ol | 142–143 |
| $N_1$—(4-fluorobenzoyl)-$N_2$—ethyl-$N_2$—phenyl-1,3-diaminopropan-2-ol | 94–96 |
| $N_1$—(4-fluorobenzoyl)-$N_2$—propyl-$N_2$—phenyl-1,3-diaminopropan-2-ol | 96–97 |
| $N_1$—(2-trifluoromethylbenzoyl)-$N_2$—methyl-$N_2$—phenyl-1,3-diaminopropan-2-ol | 96–98 |
| $N_1$—(2-trifluoromethylbenzoyl)-$N_2$—methyl-$N_2$—(4-fluorophenyl)-1,3-diaminopropan-2-ol | 88–89 |

EXAMPLE 104 according to the procedure described in Example 88, 2-chloromethyl-5-phenyloxazolidine is reacted with 2-furancarboxylic acid chloride, whereby N-furoyl-3-chloro-1-aminopropan-2-ol, having a melting point of 73°–74° C., is obtained.

According to the procedure described in Example 89, 20.4 g of the above described compound are reacted with 6.0 g of potassium hydroxide in 300 ml of tetrahydrofurane, whereby 10 g of N-(2,3-epoxypropyl)-furan-2-carboxylic acid amide are obtained as an oil. 8.2 g thereof are reacted with 8.2 g of 4-bromoaniline and 3.2 ml of glacial acetic acid according to the procedure described in Example 89. The reaction mixture is worked up as described in Example 89 and the resulting raw oil is crystallized by triturating it with ether. 6.0 g of $N_1$-furoyl-$N_2$-(4-bromophenyl)-1,3-diaminopropan-2-ol are obtained. After re-crystallization from ethylacetate/petrolether the compound exhibits a melting point of 132°–133° C.

EXAMPLE 105

A mixture of 4.8 g of $N_1$-furoyl-$N_2$-(4-bromophenyl)-1,3-diaminopropan-2-ol with 27.0 ml of formic acid and 13.5 ml of 36% formaldehyde solution, is heated on a waterbath for a period of 3.5 hours. The reaction mixture is poured onto ice and is worked up as is described in Example 91. After crystallization from isopropanol, 3.3 g of $N_1$-furoyl-$N_2$-methyl-$N_2$-(4-bromophenyl)-1,3-diaminopropan-2-ol, having a melting point of 106°–107° C., are obtained.

EXAMPLE 106

According to the procedures described in Examples 104 and 105, the $N_1$-furoyl-$N_2$-phenyl-1,3-diaminopropan-2-ol- or $N_1$-furoyl-$N_2$-alkyl-$N_2$-phenyl-1,3-diaminopropan-2-ol compounds, which are listed in Table 6 below, are prepared from N-furoyl-3-chloro-1-aminopropan-2-ol, whereby the resulting $N_1$-furoyl-$N_2$-phenyl-1,3-diaminopropan-2-ol compounds can be alkylated into the corresponding $N_1$-furoyl-$N_2$-alkyl-$N_2$-phenyl-1,3-diaminopropan-2-ol compounds.

TABLE 6

|  | Mp. °C. |
|---|---|
| $N_1$—furoyl-$N_2$—(4-chlorophenyl)-1,3-diaminopropan-2-ol | 125–127 |
| $N_1$—furoyl-$N_2$—(4-methoxyphenyl)-1,3-diaminopropan-2-ol | 113–116 |
| $N_1$—furoyl-$N_2$—methyl-$N_2$—(4-fluorophenyl)-1,3-diaminopropan-2-ol | Oil |

TABLE 6-continued

| | Mp. °C. |
|---|---|
| $N_1$—furoyl-$N_2$—methyl-$N_2$—(4-methylphenyl)-1,3-diaminopropan-2-ol | 87–88 |
| $N_1$—furoyl-$N_2$—methyl-$N_2$—(4-isopropylphenyl)-1,3-diaminopropan-2-ol | 112–113 |
| $N_1$—furoyl-$N_2$—ethyl-$N_2$—phenyl-1,3-diaminopropan-2-ol | 81–82 |
| $N_1$—furoyl-$N_2$—propyl-$N_2$—(4-chlorophenyl)-1,3-diaminopropan-2-ol | 104–105 |
| $N_1$—furoyl-$N_2$—isopropyl-$N_2$—phenyl-1,3-diaminopropan-2-ol | 89–90 |

The following examples illustrate the preparation of pharmaceutical compositions, containing a $N_1$-acyl-$N_2$-phenyl-1,3-diaminopropan-2-ol compound of formula I as a pharmacologically active ingredient:

EXAMPLE I

Capsules containing 100 mg of active ingredient per capsule.

| Composition per capsule: | |
|---|---|
| pharmacologically active ingredient | 100 mg |
| lactose | 90 mg |
| highly dispersed silicic acid (Commercial product Aerosil 200, Manufacturer Degussa) | 4 mg |
| talcum | 4 mg |
| magnesium stearate | 2 mg |
| | 200 mg |

Preparation: The pharmacologically active ingredient is thoroughly mixed with the adjuvants and the mixture is filled into gelatin capsules size #2. Capsules containing the following active ingredients are prepared according to the foregoing procedure:

$N_1$-(3,4-dimethoxybenzoyl)-$N_2$-propyl-$N_2$-(4-chlorophenyl)-1,3-diaminopropan-2-ol
$N_1$-(3,4-dimethoxybenzoyl)-$N_2$-methyl-$N_2$-(3,4-dichlorophenyl)-1,3-diaminopropan-2-ol
$N_1$-(cyclohexylcarbonyl)-$N_2$-methyl-$N_2$-(phenyl)-1,3-diaminopropan-2-ol
$N_1$-(cyclohexylcarbonyl)-$N_2$-methyl-$N_2$-(4-fluorophenyl)-1,3-diaminopropan-2-ol
$N_1$-(hexanoyl)-$N_2$-methyl-$N_2$-(4-chlorophenyl)-1,3-diaminopropan-2-ol
$N_1$-picolinoyl-$N_2$-methyl-$N_2$-(4-chlorophenyl)-1,3-diaminopropan-2-ol
$N_1$-cyclopentylcarbonyl-$N_2$-methyl-$N_2$-(4-fluorophenyl)-1,3-diaminopropan-2-ol
$N_1$-hexanoyl-$N_2$-methyl-$N_2$-(4-fluorophenyl)-1,3-diaminopropan-2-ol
$N_1$-butyryl-$N_2$-methyl-$N_2$-(4-chlorophenyl)-1,3-diaminopropan-2-ol
$N_1$-furoyl-$N_2$-methyl-$N_2$-(3,4-dichlorophenyl)-1,3-diaminopropan-2-ol

EXAMPLE II

Tablets

Tablets containing 100 mg of $N_1$-(3,4-dimethoxybenzoyl)-$N_2$-methyl-$N_2$-(4-fluorophenyl)-1,3-diaminopropan-2-ol as pharmacologically active ingredients are prepared.

| Composition per tablet: | |
|---|---|
| pharmacologically active agent | 100 mg |
| lactose | 60 mg |
| corn starch | 30 mg |
| carboxymethylcellulose (Commercial product Primojel, Manufacturer Scholtens Chemische Fabricken N.V.) | 4 mg |
| gelatin | 2 mg |
| highly dispersed silicic acid (Commercial product Aerosil 200, Manufacturer Degussa) | 2 mg |
| magnesium stearate | 2 mg |
| | 200 mg |

Preparation: A 10% mucilage of gelatin in water is prepared. The pharmacologically active agent, lactose, corn starch, and carboxymethylcellulose, are mixed, the mixture is then mixed with the mucilage and granulated through a sieve of 1.5 mm mesh-size. The granulate is dried at 40° C., once more passed through the sieve, mixed with the highly dispersed silicic acid, and the magnesium stearate and the mixture pressed into tablets using a die having a diameter of 9 mm.

The other compounds of formula I can be tabletted in the same manner.

EXAMPLE III

Coated Tablets

Coated tablets, containing 100 mg of $N_1$-(2-fluorobenzoyl)-$N_2$-methyl-$N_2$-(3,4-dichlorophenyl)-1,3-diaminopropan-2-ol as a pharmacologically active ingredient, are prepared.

According to the procedure described in Example II, tablets containing $N_1$-(2-fluorobenzoyl)-$N_2$-methyl-$N_2$-(3,4-dichlorophenyl)-1,3-diaminopropan-2-ol are prepared and subsequently are coated in a conventional manner. The resulting coated tablets are polished with the aid of beeswax.

What is claimed is:

1. A compound selected from the group of $N_1$-acyl-$N_2$-phenyl-1,3-diaminopropan-2-ols having the Formula I

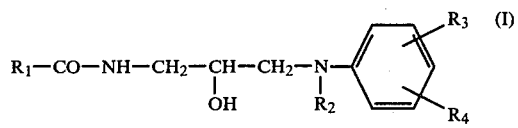

wherein
the acyl group $R_1CO$ is selected from the group consisting of acetyl, propionyl, butyryl, isobutyryl, valeryl, hexanoyl, 3,3-dimethylacryloyl, 2,2-dimethylpropionyl, isovaleryl, heptanoyl, capryloyl, 2-ethyl-hexanoyl, nonanoyl, hexadecanoyl, octadecanoyl, 6-heptenoyl, 2,4-hexendienoyl, 3-hexenoyl, cyclopropylcarbonyl, cyclobutylcarbonyl, cyclopentylcarbonyl, cyclohexylcarbonyl, 1-methylcyclohexylcarbonyl, cyclohexylacetyl, 3-cyclohexen-1-yl-carbonyl, cycloheptylcarbonyl, 1-adamantylcarbonyl, 1-adamantylacetyl, styoylcarbonyl and 3,4-dimethoxycinnamoyl;

$R_2$ represents hydrogen, alkyl containing 1 to 3 carbon atoms, or methoxyethyl, and $R_3$ and $R_4$ are the same or different from each other and each represent hydrogen, fluorine, chlorine, bromine, iodine, alkyl containing 1 to 3 carbon atoms, or alkoxy containing 1 to 3 carbon atoms;

and pharmaceutically acceptable acid addition salts thereof.

2. The compound as defined in claim 1, which is $N_1$-acetyl-$N_2$-methyl-$N_2$-phenyl-1,3-diaminopropan-2-ol and its pharmaceutically acceptable acid addition salts.

3. The compound as defined in claim 1, which is $N_1$-propionyl-$N_2$-methyl-$N_2$-phenyl-1,3-diaminopropan-2-ol and its pharmaceutically acceptable acid addition salts.

4. The compound as defined in claim 1, which is $N_1$-butyryl-$N_2$-methyl-$N_2$-phenyl-1,3-diaminopropan-2-ol and its pharmaceutically acceptable acid addition salts.

5. The compound as defined in claim 1, which is $N_1$-butyryl-$N_2$-methyl-$N_2$-(4-fluorophenyl)-1,3-diaminopropan-2-ol and its pharmaceutically acceptable acid addition salts.

6. The compound as defined in claim 1, which is $N_1$-butyryl-$N_2$-methyl-$N_2$-(4-chlorophenyl)-1,3-diaminopropan-2-ol and its pharmaceutically acceptable acid addition salts.

7. The compound as defined in claim 1, which is $N_1$-isobutyryl-$N_2$-methyl-$N_2$-(4-fluorophenyl)-1,3-diaminopropan-2-ol and its pharmaceutically acceptable acid addition salts.

8. The compound as defined in claim 1, which is $N_1$-valeryl-$N_2$-methyl-$N_2$-(4-fluorophenyl)-1,3-diaminopropan-2-ol and its pharmaceutically acceptable acid addition salts.

9. The compound as defined in claim 1, which is $N_1$-hexanoyl-$N_2$-methyl-$N_2$-phenyl-1,3-diaminopropan-2-ol and its pharmaceutically acceptable acid addition salts.

10. The compound as defined in claim 1, which is $N_1$-(3,3-dimethylacryloyl)-$N_2$-methyl-$N_2$-phenyl-1,3-diaminopropan-2-ol and its pharmaceutically acceptable acid addition salts.

11. The compound as defined in claim 1, which is $N_1$-(2,2-dimethylpropionyl)-$N_2$-methyl-$N_2$-phenyl-1,3-diaminopropan-2-ol and its pharmaceutically acceptable acid addition salts.

12. The compound as defined in claim 1, which is $N_1$-isovaleryl-$N_2$-methyl-$N_2$-(4-chlorophenyl)-1,3-diaminopropan-2-ol and its pharmaceutically acceptable acid addition salts.

13. The compound as defined in claim 1, which is $N_1$-hexanoyl-$N_2$-methyl-$N_2$-(4-chlorophenyl)-1,3-diaminopropan-2-ol and its pharmaceutically acceptable acid addition salts.

14. The compound as defined in claim 1, which is $N_1$-hexanoyl-$N_2$-methyl-$N_2$-(4-fluorophenyl)-1,3-diaminopropan-2-ol and its pharmaceutically acceptable acid addition salts.

15. The compound as defined in claim 1, which is $N_1$-heptanoyl-$N_2$-methyl-$N_2$-(4-chlorophenyl)-1,3-diaminopropan-2-ol and its pharmaceutically acceptable acid addition salts.

16. The compound as defined in claim 1, which is $N_1$-capryloyl-$N_2$-methyl-$N_2$-(4-chlorophenyl)-1,3-diaminopropan-2-ol and its pharmaceutically acceptable acid addition salts.

17. The compound as defined in claim 1, which is $N_1$-(2-ethylhexanoyl)-$N_2$-methyl-$N_2$-(4-fluorophenyl)-1,3-diaminopropan-2-ol and its pharmaceutically acceptable acid addition salts.

18. The compound as defined in claim 1, which is $N_1$-nonanoyl-$N_2$-methyl-$N_2$-(4-chlorophenyl)-1,3-diaminopropan-2-ol and its pharmaceutically acceptable acid addition salts.

19. The compound as defined in claim 1, which is $N_1$-hexadecanoyl-$N_2$-methyl-$N_2$-(4-chlorophenyl)-1,3-diaminopropan-2-ol and its pharmaceutically acceptable acid addition salts.

20. The compound as defined in claim 1, which is $N_1$-octadecanoyl-$N_2$-methyl-$N_2$-(4-chlorophenyl)-1,3-diaminopropan-2-ol and its pharmaceutically acceptable acid addition salts.

21. The compound as defined in claim 1, which is $N_1$-(6-heptenoyl)-$N_2$-methyl-$N_2$-phenyl-1,3-diaminopropan-2-ol and its pharmaceutically acceptable acid addition salts.

22. The compound as defined in claim 1, which is $N_1$-(2,4-hexendienoyl)-$N_2$-methyl-$N_2$-phenyl-1,3-diaminopropan-2-ol and its pharmaceutically acceptable acid addition salts.

23. The compound as defined in claim 1, which is $N_1$-(3-hexanoyl)-$N_2$-methyl-$N_2$-phenyl-1,3diaminopropan-2-ol and its pharmaceutically acceptable acid addition salts.

24. The compound as defined in claim 1, which is $N_1$-cyclopropylcarbonyl-$N_2$-methyl-$N_2$-phenyl-1,3-diaminopropan-2-ol and its pharmaceutically acceptable acid addition salts.

25. The compound as defined in claim 1, which is $N_1$-cyclobutylcarbonyl-$N_2$-methyl-$N_2$-phenyl-1,3-diaminopropan-2-ol and its pharmaceutically acceptable acid addition salts.

26. The compound as defined in claim 1, which is $N_1$-cyclopentylcarbonyl-$N_2$-methyl-$N_2$-phenyl-1,3-diaminopropan-2-ol and its pharmaceutically acceptable acid addition salts.

27. The compound as defined in claim 1, which is $N_1$-cyclohexylcarbonyl-$N_2$-phenyl-1,3-diaminopropan-2-ol and its pharmaceutically acceptable acid addition salts.

28. The compound as defined in claim 1, which is $N_1$-cyclohexylcarbonyl-$N_2$-(2-methylphenyl)-1,3-diaminopropan-2-ol and its pharmaceuticalldy acceptable acid addition salts.

29. The compound as defined in claim 1, which is $N_1$-cyclohexylcarbonyl-$N_2$-(3-methylphenyl)-1,3-diaminopropan-2-ol and its pharmaceutically acceptable acid addition salts.

30. The compound as defined in claim 1, which is $N_1$-cyclohexylcarbonyl-$N_2$-(2-chlorophenyl)-1,3-diaminopropan-2-ol and its pharmaceutically acceptable acid addition salts.

31. The compound as defined in claim 1, which is $N_1$-cyclohexylcarbonyl-$N_2$-(4-bromophenyl)-1,3-diaminopropan-2-ol and its pharmaceutically acceptable acid addition salts.

32. The compound as defined in claim 1, which is $N_1$-cyclohexylcarbonyl-$N_2$-(3-chloro-2-methylphenyl)-1,3-diaminopropan-2-ol and its pharmaceutically acceptable acid addition salts.

33. The compound as defined in claim 1, which is $N_1$-cyclohexylcarbonyl-$N_2$-(2,6-dimethylphenyl)-1,3-diaminopropan-2-ol and its pharmaceutically acceptable acid addition salts.

34. The compound as defined in claim 1, wherein $R_1$ is cyclohexyl, $R_2$ is methyl and the

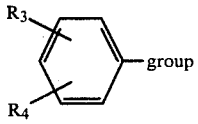

is phenyl, 4-methylphenyl, 3-chlorophenyl, 4-chlorophenyl, 4-fluorophenyl, 3,4-dichlorophenyl, 4-methoxyphenyl, or 3,4-dimethoxyphenyl.

35. The compound as defined in claim 1, wherein $R_1$ is cyclohexyl, $R_3$ and $R_4$ are hydrogen and $R_2$ is ethyl, propyl, isopropyl, or methoxyethyl.

36. The compound as defined in claim 1, which is $N_1$-(1-methylcyclohexylcarbonyl)-$N_2$-methyl-$N_2$-phenyl-1,3-diaminopropan-2-ol and its pharmaceutically acceptable acid addition salts.

37. The compound as defined in claim 1, which is $N_1$-cyclohexylacetyl-$N_2$-methyl-$N_2$-phenyl-1,3-diaminopropan-2-ol and its pharmaceutically acceptable acid addition salts.

38. The compound as defined in claim 1, which is $N_1$-cyclohexylacetyl-$N_2$-methyl-$N_2$-(3,4-dichlorophenyl)-1,3-diaminopropan-2-ol and its pharmaceutically acceptable acid addition salts.

39. The compound as defined in claim 1, which is $N_1$-(3-cyclohexen-1-yl-carbonyl)-$N_2$-methyl-$N_2$-phenyl-1,3-diaminopropan-2-ol and its pharmaceutically acceptable acid addition salts.

40. The compound as defined in claim 1, which is $N_1$-cycloheptylcarbonyl-$N_2$-methyl-$N_2$-phenyl-1,3-diaminopropan-2-ol and its pharmaceutically acceptable acid addition salts.

41. The compound as defined in claim 1, which is $N_1$-(1-adamantylcarbonyl)-$N_2$-methyl-$N_2$-phenyl-1,3-diaminopropan-2-ol and its pharmaceutically acceptable acid addition salts.

42. The compound as defined in claim 1, which is $N_1$-(1-adamantylacetyl)-$N_2$-methyl-$N_2$-phenyl-1,3-diaminopropan-2-ol and its pharmaceutically acceptable acid addition salts.

43. The compound as defined in claim 1, which is $N_1$-(1-adamantylacetyl)-$N_2$-methyl-$N_2$-(4-chlorophenyl)-1,3-diaminopropan-2-ol and its pharmaceutically acceptable acid addition salts.

44. The compound as defined in claim 1, wherein $R_1$ is styryl, $R_2$ is methyl, and the

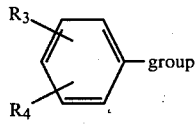

is phenyl, 4-fluorophenyl, or 4-chlorophenyl.

45. The compound as defined in claim 1, which is $N_1$-(3,4-dimethoxycinnamoyl)-$N_2$-methyl-$N_2$-(4-chlorophenyl-1,3-diaminopropan-2-ol and its pharmaceutically acceptable acid addition salts.

46. A method of treating disorders which are connected with the formation of ulcers in larger mammals, which comprises the step of administering to a larger mammal an ulcer-inhibiting effective amount of at least one compound, as defined in claim 1.

47. The method as defined in claim 46, wherein the amount of the pharmacologically active compound is from about 150 to about 450 mg per day.

* * * * *